(12) United States Patent
Paya Cuenca et al.

(10) Patent No.: US 8,962,593 B2
(45) Date of Patent: *Feb. 24, 2015

(54) GLA MONOTHERAPY FOR USE IN CANCER TREATMENT

(71) Applicant: Immune Design Corp., Seattle, WA (US)

(72) Inventors: Carlos V. Paya Cuenca, San Francisco, CA (US); Jan Henrik Ter Meulen, Mercer Island, WA (US)

(73) Assignee: Immune Design Corp., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/333,758

(22) Filed: Jul. 17, 2014

(65) Prior Publication Data

US 2014/0328904 A1 Nov. 6, 2014

Related U.S. Application Data

(63) Continuation of application No. 14/256,521, filed on Apr. 18, 2014.

(60) Provisional application No. 61/946,317, filed on Feb. 28, 2014, provisional application No. 61/891,609, filed on Oct. 16, 2013, provisional application No. 61/834,415, filed on Jun. 12, 2013, provisional application No. 61/826,311, filed on May 22, 2013, provisional application No. 61/813,499, filed on Apr. 18, 2013.

(51) Int. Cl.
| | | |
|---|---|---|
| *A61K 31/715* | (2006.01) | |
| *A61K 31/7024* | (2006.01) | |
| *A61K 39/395* | (2006.01) | |
| *A61K 45/06* | (2006.01) | |
| *A61N 5/10* | (2006.01) | |

(52) U.S. Cl.
CPC ....... *A61K 31/7024* (2013.01); *A61K 39/39558* (2013.01); *A61K 45/06* (2013.01); *A61N 5/10* (2013.01)
USPC .......................................................... 514/53

(58) Field of Classification Search
None
See application file for complete search history.

(56) References Cited

U.S. PATENT DOCUMENTS

| | | |
|---|---|---|
| 3,238,190 A | 3/1966 | Erbring et al. |
| 3,598,122 A | 8/1971 | Zaffaroni |
| 3,598,123 A | 8/1971 | Zaffaroni |
| 4,029,762 A | 6/1977 | Galanos et al. |
| 4,286,592 A | 9/1981 | Chandrasekaran |
| 4,314,557 A | 2/1982 | Chandrasekaran |
| 4,379,454 A | 4/1983 | Campbell et al. |
| 4,420,461 A | 12/1983 | Reckel et al. |
| 4,420,558 A | 12/1983 | De Mey et al. |
| 4,435,386 A | 3/1984 | Ribi et al. |
| 4,436,728 A | 3/1984 | Ribi et al. |
| 4,568,343 A | 2/1986 | Leeper et al. |
| 4,595,654 A | 6/1986 | Reckel et al. |
| 4,614,722 A | 9/1986 | Pasula |
| 4,629,722 A | 12/1986 | Ribi |
| 4,659,659 A | 4/1987 | Dwek et al. |
| 4,663,306 A | 5/1987 | Cantrell |
| 4,743,540 A | 5/1988 | Ralph et al. |
| 4,767,402 A | 8/1988 | Kost et al. |
| 4,769,330 A | 9/1988 | Paoletti et al. |
| 4,780,212 A | 10/1988 | Kost et al. |
| 4,844,894 A | 7/1989 | Ribi |
| 4,897,268 A | 1/1990 | Tice et al. |
| 4,912,094 A | 3/1990 | Myers et al. |
| 4,948,587 A | 8/1990 | Kost et al. |
| 4,981,684 A | 1/1991 | MacKenzie et al. |
| 4,987,237 A | 1/1991 | Myers et al. |
| 5,017,487 A | 5/1991 | Stunnenberg et al. |
| 5,057,540 A | 10/1991 | Kensil et al. |
| 5,075,109 A | 12/1991 | Tice et al. |
| 5,124,141 A | 6/1992 | Makler |
| 5,147,785 A | 9/1992 | Pasula |
| 5,162,990 A | 11/1992 | Odeyale et al. |
| 5,231,168 A | 7/1993 | Dziegiel et al. |
| 5,278,302 A | 1/1994 | Caruthers et al. |
| 5,298,396 A | 3/1994 | Kotzin et al. |
| 5,411,865 A | 5/1995 | Reed |
| 5,422,109 A | 6/1995 | Brancq et al. |
| 5,424,067 A | 6/1995 | Brancq et al. |
| 5,457,041 A | 10/1995 | Ginaven et al. |
| 5,464,387 A | 11/1995 | Haak et al. |
| 5,530,113 A | 6/1996 | Christ et al. |
| 5,591,139 A | 1/1997 | Lin et al. |

(Continued)

FOREIGN PATENT DOCUMENTS

| | | |
|---|---|---|
| DE | 3833319 A1 | 4/1989 |
| EP | 0109942 A2 | 5/1984 |

(Continued)

OTHER PUBLICATIONS

Anderson et al., Physicochemical characterization and biological activity of synthetic TLR4 agonist formulation, *Colloids and Surfaces Biointerfaces*, 75(1):130 (2010).

Garay et al., Cancer relapse under chemotherapy: Why TLR2/4 receptor agonists can help, *Europ. J. Pharmacol.*,563(1-3):1-17 (2007).

Hsiao et al., Toll-Like receptor-4 agonist inhibits motility and invasion of hepatoblastoma HepG2 cells in vitro, *Ped. Blood & Cancer*, 60(2):252 (2012).

Kastenmuller et al., Full length *Plasmodium falciparum* Circumsporozite Protein Administered with Long-Chain Poly (IC) or the Toll-Like Receptor 4 Agonist Glucopyranosy Lipid Adjuvant-Stable Emulsion Elicits Potent Antibody and CD4+ T Cell Immunity and Protection in Mice, *Infection and Immunity*, 81(3):789-800 (2012).

(Continued)

*Primary Examiner* — Traviss C McIntosh, III
(74) *Attorney, Agent, or Firm* — Marshall, Gerstein & Borun LLP

(57) ABSTRACT

The present disclosure relates generally to compositions and methods for treating cancer with a glucopyranosyl lipid A (GLA) in the absence of antigen.

18 Claims, 10 Drawing Sheets

(56) References Cited

U.S. PATENT DOCUMENTS

| | | | |
|---|---|---|---|
| 5,595,888 A | 1/1997 | Gray et al. |
| 5,612,041 A | 3/1997 | Burke et al. |
| 5,612,476 A | 3/1997 | Christ et al. |
| 5,618,275 A | 4/1997 | Bock |
| 5,650,155 A | 7/1997 | Cornelius et al. |
| 5,654,140 A | 8/1997 | Persico et al. |
| 5,656,016 A | 8/1997 | Ogden |
| 5,666,153 A | 9/1997 | Copeland |
| 5,667,784 A | 9/1997 | Cornelius et al. |
| 5,693,531 A | 12/1997 | Chiorini et al. |
| 5,718,904 A | 2/1998 | Hjorth |
| 5,719,263 A | 2/1998 | Reed |
| 5,722,397 A | 3/1998 | Eppstein |
| 5,756,718 A | 5/1998 | Christ et al. |
| 5,776,468 A | 7/1998 | Hauser et al. |
| 5,786,148 A | 7/1998 | Bandman et al. |
| 5,795,577 A | 8/1998 | Kieny et al. |
| 5,840,871 A | 11/1998 | Hillman et al. |
| 5,843,464 A | 12/1998 | Bakaletz et al. |
| 5,843,918 A | 12/1998 | Christ et al. |
| 5,846,758 A | 12/1998 | Medenica |
| 5,885,211 A | 3/1999 | Eppstein et al. |
| 5,888,519 A | 3/1999 | Alving |
| 5,912,166 A | 6/1999 | Reed et al. |
| 5,952,309 A | 9/1999 | Rossignol et al. |
| 5,955,306 A | 9/1999 | Gimeno et al. |
| 5,976,538 A | 11/1999 | Hilgers et al. |
| 5,981,215 A | 11/1999 | Meissner et al. |
| 5,993,800 A | 11/1999 | Linsley et al. |
| 6,005,099 A | 12/1999 | Davies et al. |
| 6,027,730 A | 2/2000 | Francotte et al. |
| 6,027,732 A | 2/2000 | Morein et al. |
| 6,033,928 A | 3/2000 | Eriguchi et al. |
| 6,057,427 A | 5/2000 | Smith et al. |
| 6,106,824 A | 8/2000 | Kaplitt et al. |
| 6,120,769 A | 9/2000 | Gefter et al. |
| 6,146,632 A | 11/2000 | Momin et al. |
| 6,212,102 B1 | 4/2001 | Georgakos et al. |
| 6,218,186 B1 | 4/2001 | Choi et al. |
| 6,231,861 B1 | 5/2001 | Barnwell |
| 6,235,724 B1 | 5/2001 | Asai et al. |
| 6,261,762 B1 | 7/2001 | Alizon et al. |
| 6,270,769 B1 | 8/2001 | Raychaudhuri et al. |
| 6,309,847 B1 | 10/2001 | Cohen et al. |
| 6,316,183 B1 | 11/2001 | Alizon et al. |
| 6,322,532 B1 | 11/2001 | D'Sa et al. |
| 6,375,944 B1 | 4/2002 | Trinchieri et al. |
| 6,472,515 B1 | 10/2002 | Climent-Johansson et al. |
| 6,488,936 B1 | 12/2002 | Mishkin et al. |
| 6,491,919 B2 | 12/2002 | Crane |
| 6,512,102 B1 | 1/2003 | Xu et al. |
| 6,544,518 B1 | 4/2003 | Gerard et al. |
| 6,544,728 B1 | 4/2003 | Alizon et al. |
| 6,555,653 B2 | 4/2003 | Alderson et al. |
| 6,572,861 B1 | 6/2003 | Roberts et al. |
| 6,587,792 B1 | 7/2003 | Thomas |
| 6,596,501 B2 | 7/2003 | Roth |
| 6,613,892 B2 | 9/2003 | Preston et al. |
| 6,630,161 B1 | 10/2003 | Leesman |
| 6,654,462 B1 | 11/2003 | Hedberg |
| 6,660,487 B2 | 12/2003 | Faustman |
| 6,676,961 B1 | 1/2004 | Lichter |
| 6,682,901 B2 | 1/2004 | Blaschuk et al. |
| 6,685,699 B1 | 2/2004 | Eppstein et al. |
| 6,692,752 B1 | 2/2004 | Slaoui et al. |
| 6,706,872 B1 | 3/2004 | Barnwell |
| 6,713,068 B1 | 3/2004 | Audonnet et al. |
| 6,733,763 B2 | 5/2004 | Raychaudhuri et al. |
| 6,749,856 B1 | 6/2004 | Berzofsky et al. |
| 6,752,995 B2 | 6/2004 | Johnston et al. |
| 6,770,445 B1 | 8/2004 | Scholler et al. |
| 6,783,981 B1 | 8/2004 | Uden et al. |
| 6,797,276 B1 | 9/2004 | Glenn et al. |
| 6,828,155 B1 | 12/2004 | Kaneko et al. |
| 6,844,192 B2 | 1/2005 | Orlando et al. |
| 6,846,489 B1 | 1/2005 | Garcon et al. |
| 6,846,648 B2 | 1/2005 | Maes |
| 6,855,322 B2 | 2/2005 | Lyon et al. |
| 6,869,607 B1 | 3/2005 | Buschle et al. |
| 6,871,477 B1 | 3/2005 | Tucker |
| 6,875,610 B2 | 4/2005 | Higginbotham et al. |
| 6,893,820 B1 | 5/2005 | Plass |
| 6,908,453 B2 | 6/2005 | Fleming et al. |
| 6,911,434 B2 | 6/2005 | Baldridge et al. |
| 6,919,078 B2 | 7/2005 | Ni et al. |
| 6,929,796 B1 | 8/2005 | Conti-Fine |
| 6,932,972 B2 | 8/2005 | Stephenne et al. |
| 6,933,123 B2 | 8/2005 | Hu et al. |
| 6,936,255 B1 | 8/2005 | Wettendorff |
| 6,949,246 B2 | 9/2005 | Reed et al. |
| 6,969,704 B1 | 11/2005 | Pinsky et al. |
| 6,970,739 B1 | 11/2005 | Inoue |
| 6,974,588 B1 | 12/2005 | Miranda et al. |
| 6,977,073 B1 | 12/2005 | Cezayirli et al. |
| 6,979,535 B2 | 12/2005 | Alizon et al. |
| 6,979,730 B2 | 12/2005 | Reiter et al. |
| 6,991,791 B2 | 1/2006 | Le et al. |
| 7,001,770 B1 | 2/2006 | Atencio et al. |
| 7,008,774 B2 | 3/2006 | Ryan et al. |
| 7,012,134 B2 | 3/2006 | Ruben et al. |
| 7,018,345 B2 | 3/2006 | Mori et al. |
| 7,029,678 B2 | 4/2006 | Momin et al. |
| 7,029,685 B2 | 4/2006 | Lanar et al. |
| 7,030,232 B1 | 4/2006 | Reiter et al. |
| 7,033,598 B2 | 4/2006 | Lerner |
| 7,037,712 B2 | 5/2006 | Both et al. |
| 7,052,904 B2 | 5/2006 | Zheng et al. |
| 7,060,276 B2 | 6/2006 | Lanar et al. |
| 7,060,802 B1 | 6/2006 | Trakht et al. |
| 7,067,310 B2 | 6/2006 | Chartier et al. |
| 7,078,180 B2 | 7/2006 | Genetta |
| 7,084,256 B2 | 8/2006 | McCormick et al. |
| 7,087,231 B2 | 8/2006 | Guerin-Marchand et al. |
| 7,087,713 B2 | 8/2006 | Campos-Neto et al. |
| 7,357,936 B1 | 4/2008 | Garcon |
| 7,820,627 B2 | 10/2010 | Jiang et al. |
| 8,273,361 B2 * | 9/2012 | Reed et al. ............... 424/282.1 |
| 8,343,512 B2 | 1/2013 | Reed et al. |
| 2002/0176867 A1 | 11/2002 | Andersen et al. |
| 2003/0165512 A1 | 9/2003 | Wheeler et al. |
| 2003/0170249 A1 | 9/2003 | Hakomori et al. |
| 2003/0194391 A1 | 10/2003 | Ashman et al. |
| 2003/0215497 A1 | 11/2003 | Leesman |
| 2004/0120924 A1 | 6/2004 | Hone et al. |
| 2004/0161776 A1 | 8/2004 | Maddon et al. |
| 2005/0123550 A1 | 6/2005 | Laurent et al. |
| 2007/0072824 A1 | 3/2007 | Kawano et al. |
| 2008/0131466 A1 | 6/2008 | Reed et al. |
| 2009/0181078 A1 | 7/2009 | Reed et al. |
| 2010/0310602 A1 | 12/2010 | Reed et al. |
| 2011/0014274 A1 | 1/2011 | Reed et al. |
| 2011/0070290 A1 | 3/2011 | Reed et al. |
| 2012/0039994 A1 | 2/2012 | Reed et al. |

FOREIGN PATENT DOCUMENTS

| | | |
|---|---|---|
| EP | 0198474 A1 | 10/1986 |
| EP | 0224260 A2 | 6/1987 |
| EP | 0304578 A1 | 3/1989 |
| EP | 0324455 A2 | 7/1989 |
| EP | 0362279 A1 | 4/1990 |
| EP | 0366412 A2 | 5/1990 |
| EP | 0382271 A1 | 8/1990 |
| EP | 0414374 A2 | 2/1991 |
| EP | 0468520 A2 | 1/1992 |
| EP | 0761231 A1 | 3/1997 |
| EP | 0729473 B1 | 8/2000 |
| EP | 1531158 A1 | 5/2005 |
| EP | 2068918 B1 | 5/2012 |
| GB | 2220211 A | 1/1990 |
| GB | 2232892 A | 1/1991 |
| JP | 63010728 A | 1/1988 |
| JP | 07055906 B2 | 6/1995 |
| JP | 10131046 A | 5/1998 |

(56) References Cited

FOREIGN PATENT DOCUMENTS

| | | |
|---|---|---|
| WO | WO-89/01973 A2 | 3/1989 |
| WO | WO-90/01496 A1 | 2/1990 |
| WO | WO-90/06951 A1 | 6/1990 |
| WO | WO-90/07936 A1 | 7/1990 |
| WO | WO-91/00106 A1 | 1/1991 |
| WO | WO-91/00107 A1 | 1/1991 |
| WO | WO-91/02805 A2 | 3/1991 |
| WO | WO-93/02184 A1 | 2/1993 |
| WO | WO-93/10152 A1 | 5/1993 |
| WO | WO-93/12778 A1 | 7/1993 |
| WO | WO-93/25234 A1 | 12/1993 |
| WO | WO-93/25698 A1 | 12/1993 |
| WO | WO-94/00152 A1 | 1/1994 |
| WO | WO-94/00153 A1 | 1/1994 |
| WO | WO-94/03622 A1 | 2/1994 |
| WO | WO-94/05792 A1 | 3/1994 |
| WO | WO-94/20137 A1 | 9/1994 |
| WO | WO-94/21292 A1 | 9/1994 |
| WO | WO-95/14026 A1 | 5/1995 |
| WO | WO-95/17209 A1 | 6/1995 |
| WO | WO-95/17210 A1 | 6/1995 |
| WO | WO-95/20600 A1 | 8/1995 |
| WO | WO-95/26204 A1 | 10/1995 |
| WO | WO-96/02555 A1 | 2/1996 |
| WO | WO-96/09310 A1 | 3/1996 |
| WO | WO-96/11272 A2 | 4/1996 |
| WO | WO-96/11711 A1 | 4/1996 |
| WO | WO-96/26277 A1 | 8/1996 |
| WO | WO-96/33739 A1 | 10/1996 |
| WO | WO-97/11708 A1 | 4/1997 |
| WO | WO-97/42947 A1 | 11/1997 |
| WO | WO-98/01139 A1 | 1/1998 |
| WO | WO-98/12302 A1 | 3/1998 |
| WO | WO-98/16247 A1 | 4/1998 |
| WO | WO-98/20117 A1 | 5/1998 |
| WO | WO-98/37418 A2 | 8/1998 |
| WO | WO-98/43670 A2 | 10/1998 |
| WO | WO-98/56414 A1 | 12/1998 |
| WO | WO-98/58956 A2 | 12/1998 |
| WO | WO-99/03884 A2 | 1/1999 |
| WO | WO-99/10375 A2 | 3/1999 |
| WO | WO-99/11241 A1 | 3/1999 |
| WO | WO-99/12565 A1 | 3/1999 |
| WO | WO-99/17741 A1 | 4/1999 |
| WO | WO-99/28475 A2 | 6/1999 |
| WO | WO-99/40188 A2 | 8/1999 |
| WO | WO-99/51748 A2 | 10/1999 |
| WO | WO-99/53061 A2 | 10/1999 |
| WO | WO-00/04149 A2 | 1/2000 |
| WO | WO-00/13029 A1 | 3/2000 |
| WO | WO-00/18929 A2 | 4/2000 |
| WO | WO-00/25815 A1 | 5/2000 |
| WO | WO-00/42994 A2 | 7/2000 |
| WO | WO-01/36433 A2 | 5/2001 |
| WO | WO-01/90129 A2 | 11/2001 |
| WO | WO-02/16560 A1 | 2/2002 |
| WO | WO-02/28424 A2 | 4/2002 |
| WO | WO-02/32450 A2 | 4/2002 |
| WO | WO-02/32454 A1 | 4/2002 |
| WO | WO-03/094850 A2 | 11/2003 |
| WO | WO-2006/055729 A1 | 5/2006 |
| WO | WO-2008/153541 A1 | 12/2008 |
| WO | WO-2009/035528 A2 | 3/2009 |
| WO | WO-2009/143457 A2 | 11/2009 |
| WO | WO-2010/141861 A1 | 12/2010 |
| WO | WO-2012/009611 A2 | 1/2012 |
| WO | WO-2013/119856 A1 | 8/2013 |

OTHER PUBLICATIONS

Koido et al., The combination of TLR2 and TLR4 agonists promotes the immunogenicity of dendritic cell/cancer cell fusions, *Oncoimmunology*, 2(7):e24660-2 (2013).

Lin et al., In vitro and in vivo anticancer activity of a synthetic glycolipid as a toll-like receptor 4 (TLR4) activator, *J. Biol. Chem.*, 286(51):43782-92 (2011).

Wang et al., Effective antibody therapy induces host-protective antitumor immunity that is augmented by TLR 4 agonist treatment, *Canc. Immunol. Immunother.*, 61(1):49-61 (2011).

Yusuf et al., Protective role of Toll-like Receptor 4 during the Initiation Stage of cutaneous Chemical Carcinogenesis, *Cancer Res.*, 68(2):615-22 (2008).

International Search Report and Written Opinion of the International Searching Authority, European Patent Office, PCT/US2014/034654, dated Jul. 25, 2014.

Ahmed et al., Links between toll-like receptor 4 and breast cancer, *OncoImmunol.* 2(2): e22945-1-e22945-7 (2013).

Akamatsu et al., Synthesis of lipid A monosaccharide analogues containing acidic amino acid: Exploring the structural basis for the endotoxic and antagonistic activities, *Bioorg. Med. Chem.*, 14:6759-77 (2006).

Akamizu et al., Molecular analysis of stimulatory anti-thyrotropin receptor antibodies (TSAbs) involved in Graves' Disease, *J. Immunol.*, 157(7):3148-52 (1996).

Alexander et al., Bacterial lipopolysaccharides and innate immunity, *J. Endotoxin Res.*, 7(3):167-202 (2001).

Alving et al., Lipid A and liposomes containing lipid a as antigens and adjuvants, *Vaccine*, 26:3036-45 (2008).

Alving, Lipopolysaccharide, Lipid A, and liposomes containing lipid A as immunologic adjuvants, *Immunobiol.*, 187:430-46 (1993).

American Thoracic Society, Standards for the diagnosis and care of patients with Chronic Obstructive Pulmonary Disease, *Am. J. Respir. Crit. Care Med.*, 152(5 Pt 2):577-S121 (1995).

Amos et al., Adoptive immunotherapy combined with intratumoral TLR agonist delivery eradicates established melanoma in mice. *Cancer Immunol. Immunother.* 60(5): 671-83 (2011).

Andaloussi et al., Stimulation of TLR9 with CpG ODN enhances apoptosis of glioma and prolongs the survival of mice with experimental brain tumors, *Glia*, 54(6):526-35 (2006).

Apicella et al., Antigenic heterogeneity of lipid A of *Haemophilus imfluenzae*, *Infect. Immun.*, 50:9-14 (1985).

Armant et al., Toll-like Receptors: a family of pattern-recognition receptors in mammals, *Genome Biol.*, 3(8):3011.1-.6 (2002).

Asai, Development of an injectable formulation for the novel Lipid A analog E5531 using a pH-jump method, *Yakugaku Zasshi*, 24(12):965-72 (2004).

Avanti Polar Lipids, Certificate of Analysis #770030-Monophosphoryl Lipid A (Synthetic cGMP) Dated Jan. 15, 2008.

Avanti Polar Lipids, Inc., Product Data Sheet for Avanti Product No. 699200, Lipid A—Purified Detoxified Lipid A, http://www.avantilipds.com, download date Jan. 14, 2009.

Avanti Polar Lipids, Inc., Product Data Sheet for Avanti Product No. 699800, Lipid(Synthetic)(PHAD™) Monophosphoryl Lipid A (Synthetic)(PHAD™) http://www.avantilipds.com, download date Jan. 14, 2009.

Avanti, Advertising: Synthetic Adjuvant, J. Immunol., [Online] 178(10):1-5, May 15, 2007; XP002546530.

Avanti, Advertising: The New PHAD ™ in vaccine technology Avanti's Synthetic Vaccine Adjuvant, J. Immunol., [Online] 179(12): 1-6, Dec. 15, 2007; XP002546531.

Badaro et al., Evaluation of micro enzyme-linked Immunosorbent Assay (ELISA) for antibodies in American Visceral Leishmaniasis: antigen selection for detection of infection-specific responses, *Am. J. Trop. Med. Hyg.*, 35:72-8 (1986).

Badaro et al., rK39: A cloned antigen of *Leishmania chagasi* that predicts active visceral leishmaniasis, *J. Infect. Dis.*, 173(3):758-61 (1996).

Bainbridge et al., Expression of a *Porphyromonas gingivalis* lipid A palmitylacyl transferase in *Escherichia coli* yields a chimeric lipid A with altered ability to stimulate interleukin-8 secretion, *Cell Microbiol.*, 8(1):120-9 (2006).

Baldridge et al., Monophosphoryl lipid A (MPL) formulations for the next generation of vaccines, *Methods*, 19:103-7 (1999).

Baldridge et al., Monophosphoryl lipid A enhances mucosol and systemic immunity to vaccine antigens following intranasal administration, *Vaccine*, 18:2416-25 (2000).

Baldridge et al., Taking a toll on human disease: Toll-like receptor 4 agonists as vaccine adjuvants and monotherapeutic agents, *Exp. Opin. Biol. Ther.* 4(7): 1129-38 (2004).

(56) References Cited

OTHER PUBLICATIONS

Bardou et al., Antitumoral Effects of Lipids A, Clinical Studies, in Lipid A in Cancer Therapy, Chapter 11, p. 125-31 (2009).
Bayes et al., Gateways to clinical trials, *Methods Exp. Clin. Pharmacol.*, 27(3):193-219 (2005).
Berkner, Development of adenovirus vectors for the expression of heterologous genes, *Biotechniques*, 6(7):616-27 (1988).
Bertholet et al., Optimized subunit vaccine protects against experimental *leishmaniasis*, *Vaccine*, 27(50):7036-45 (2009).
Bomford et al., Adjuvanticity and ISCOM formation by structurally diverse saponins, *Vaccine*, 10(9):572-7 (1992).
Borges et al., Potent stimulation of the innate immune system by a *Leishmania brasiliensis* recombinant protein, *Infect. Immun.*, 69(9):5270-7 (2001).
Bortolatto et al., Toll-Like receptor 4 agonists adsorbed to aluminum hydroxide adjuvant attenuate ovalbumin-specific allergic airway disease: Role of MyD88 adaptor molecule and interleukin-12/interferon-y axis, *Clin. Exper. Allergy*, 38:1668-79 (2008).
Brade et al., Immunogenicity and antigenicity of synthetic *Escherichia coli* Lipid A, *Infect. Immunity*, 51(1):110-4 (1986).
Brade et al., The Immunogenicity and Antigenicity of Lipid A are influenced by its physicochemical state and environment, *Infect. Immunity*, 55(11):2636-44 (1987).
Brandenberg, Fourier transform infrared spectroscopy characterization of the lamellar and nonlamellar structures of free lipid A and Re lipopolysaccharides from *Salmonella minnesota* and *Escherichia coli*, *Bioohys. J.*, 64:1215-31 (1993).
Brandenburg et al., Conformational studies of synthetic lipid A analogues and partial structures by infrared spectroscopy, *Biochim. Biophys. Acta*, 1329:183-201 (1997).
Brandenburg et al., Endotoxins: relationships between structure, function, and activity, *Curr. Topics Med. Chem.* 4(1 1):1127-46 (2004).
Brandenburg et al., Physicochemical characteristics of triacyl lipid A partial structure OM-174 in relation to biological activity, *Eur. J. Biochem.*, 267:3370-7 (2000).
Bray et al., The immunology and serology of leishmaniasis. iv. result of ouchterlony double diffusion tests, *Trans. R. Soc. Trop. Med. Hyg.*, 60(5):605-9 (1966).
Brazolot et al., CpG DNA can induce strong Th1 humoral and cell mediated immune responses against hepatitis B surface antigen in young mice, *Proc. Natl. Acad. Sci. USA*, 95(26):15553-8 (1998).
Bulusu et al., Acyclic analogs of lipid A: synthesis and biological activities, *J. Med. Chem.*, 35(19):3463-9 (1992).
Burrell, Immunomodulation by bacterial endotoxin, *Microbiology*, 17(3):189-208 (1990).
Cady et al., Somnogenic activities of synthetic Lipid A, *Infect. Immunity*, 57(2):396-403 (1989).
Campagnari et al., Role of lipooligosaccharides in experimental dermal lesions caused by *Haemophilus ducreyi*, *Infect. Immun.*, 59:2601-8 (1991).
Casale et al., Safety of the intranasal toll-like receptor 4 agonist CRX-675 in allergic rhinitis, *Asthma Immunol.* 97(4):454-6 (2006).
Casella et al., Putting endotoxin to work for us: Monophosphoryl lipid A as a safe and effective vaccine adjuvant, *Cell Mol. Life Sci.*, 65:3231-40 (2008).
Chen et al., Distinct responses of lung and spleen dendritic cells to the TLR9 Against CpG oligodeoxynucleotide, *J. Immunol.*, 177(4):2373-83 (2006).
Choudhary et al., An Indirect Fluorescent Antibody (IFA) test for the serodiagnosis of Kala-Azar, *J. Comm. Dis.*, 24(1):32-6 (1992).
Choudhary et al., Enzyme-linked immunosorbent assay in the diagnosis of Kala-azar in Bhadohi (Varanasi), India, *Trans. R. Soc. Trop. Med. Hyg.*, 84(3):363-6 (1990).
Ciprandi et al., Emerging anti-inflammatory agents for allergic rhinitis, *Exp. Opin. Emerg. Drugs*, 10(4):689-705 (2005).
Coler et al., Immunization with a polyprotein vaccine consisting of the t-cell antigens thiol-specific antioxidant, *Leishmania major* stress-inducible protein 1, and *Leishmania* elongation initiation factor protects against leishmaniasis, *Infect. Immunity*, 70(8):4215-25 (2002).
Cooper et al., CPG 7909 Adjuvant improves Hepatitis B virus vaccine seroprotection in antiretroviral-treated HIV-infected adults, *AIDS*, 19(14):1473-9 (2005).
Correale et al., In vitro generation of human cytotoxic t lymphocytes specific for peptides derived from prostate-specific antigen, *J. National Cancer Institute*, 89(4):293-300 (1997).
Cotten et al., High-efficiency receptor-mediated delivery of small and large (48 Kilobase Gene Constructs Using the Endosome-Disruption Activity of Defective or Chemically Inactivated Adenovirus Particles), *Proc. Natl. Acad. Sci. USA*, 89(13):6094-8 (1992).
Curiel et al., High efficiency gene transfer mediated by adenovirus coupled to DNA-polylysine complexes, *Hum. Gene Ther.*, 3(2):147-54 (1992).
D'Agostini et al., Antitumor effect of OM-174 and cyclophosphamide on murine B16 melanoma in different experimental conditions. *Intl. Immunopharmacol.* 5: 1205-12 (2005).
Darveau et al., Lipid A diversity and the innate host response to bacterial infection, *Curr. Opin. Microbiol.*, 1:36-42 (1998).
Datta et al., A Subset of Toll-Like Receptor ligands induces cross-presentation by bone marrow-derived dendritic cells, *J. Immunol.*, 170(8):4102-10 (2003).
Davis et al., CpG DNA is a potent enhancer of specific immunity in mice immunized with recombinant Hepatitis B surface antigen, *J. Immunol.*, 160(2):870-6 (1998).
Davis et al., Intratumoral administration of TLR4 agonist absorbed into a cellular vector improves antitumor responses. *Clin. Cancer Res.* 17: 3984-92 (2011).
de Bono et al., Phase I study of ONO-4007, a synthetic analogue of the lipid A moiety of bacterial lipopolysaccharide, *Clin. Cancer Res.* 6: 397-405 (2000).
Declaration of Dr. David T. Hickman submitted in support of opposition of European Patent No. EP-2068918 B1, dated Jan. 31, 2013.
Declaration of Dr. Maria Pilar Lopez-Deber submitted in support of opposition of European Patent No. EP-2068918 B1, dated Jan. 31, 2013.
Deng et al., CpG oligodeoxynucleotides stimulate protective innate immunity against pulmonary klebsiella infection, *J. Immunol.*, 173:5148-55 (2004).
Diks et al., LPS signal transduction: The picture is becoming more complex, *Curr. Topics Med. Chem.*, 4:1115-26 (2004).
Dixon et al., Lipopolysaccharide heterogeneity: Innate host responses to bacterial modification of Lipid A structure, *J. Dent Res.*, 84(7):584-95 (2005).
Edelman, The development and use of vaccine adjuvants, *Mol. Biotechnol.*, 21(2):129-48 (2002).
Edelman, Vaccine adjuvants, *Rev. Infect. Dis.*, 2(3):370-83 (1980).
El-On et al., *Leishmania donovani*: Physicochemical, immunological, and biological characterization of excreted factor from promastigotes, *Exper. Parasitol.*, 47(2):254-69 (1979).
European Application No. 07 875 082.5, Office Action mailed Feb. 2, 2010.
Fearon et al., The instructive role of innate immunity in the acquired immune response, *Science*, 272(5258):50-4 (1996).
Feigner et al., Lipofection: A highly efficient, lipid-mediated DNA-transfection procedure, *Proc. Natl. Acad. Sci. USA*, 84(21):7413-7 (1987).
Feuillet et al., Involvement of toll-like receptor 5 in the recognition of flagellated bacteria, *Proc. Natl. Acad. Sci. USA*, 103(33):12487-92 (2006).
Flad et al., Interleukin 1 and tumor necrosis factor: Studies on the induction by lipopolysaccharide partial structures, *Lymphokine Research*, 8(3): 235-8 (1989).
Flesher et al., Characterization of lipopolysaccharide of *Haemophilus influenzae*, *J. Infect. Dis.*, 138:719-30 (1978).
Fujimoto et al., Synthesis of lipid A and its analogues for investigation of the structural basis for their bioactivity, *J. Endotoxin Res.*, 11(6):341-7 (2005).

(56) References Cited

OTHER PUBLICATIONS

Funatogawa et al., Relationship of structure and biological activity of monosaccharide lipid A analogues to induction of nitric oxide production by murine macrophase RAW264.7 cells, *Infect. Immun.*, 5792-8 (1998).
Galanos et al., Endotoxic properties of chemically synthesized lipid A part structures, *Eur. J. Biochem.*, 140:221-7 (1984).
Galanos et al., Synthetic and natural *Escherichia coli* free lipid A express identical endotoxic activities, *Eur. J. Biochem.*, 148:1-5, (1985).
Garcon, Preclinical development of A504, *Methods in Molecular Biology*, 626:15-27 (2010).
Garidel et al., Divalent cations affect chain mobility and aggregate structure of lipopolysaccharide from *Salmonella minnesota* reflected in a decrease of its biological activity, *Biochim. Biophys. Acta*, 17:122-31 (2005).
Gatouillat et al., Immunization with liposome-anchored pegylated peptides modulates doxorubicin sensitivity in P-glycoprotein-expressing P388 cells. *Cancer Lett.* 257: 165-71 (2007).
Gibson et al., Plasmacytoid dendritic cells produce cytokines and mature in response to the TLR7 agonists, imiquimod and resiquimod, *Cell. Immunol.*, 218(1-2):74-86 (2002).
Gisvold, Digitonin and phytosterol from the seed of *Digitalis purpurea*, *Phytochem. Notes Amer. Pharmacol. Assoc.*, 23(7):664-6 (1934).
Gluck, Immunopotentiating Reconstituted Influenza Virosomes (IRIVs) and other adjuvants for improved presentation of small antigens, *Vaccine*, 10(13):915-9 (1992).
Goldman, Translational mini-review series on toll-like receptors: Toll-like receptor ligands as novel pharmaceuticals for allergic disorders, *Clin. Exper. Immunol.*, 147:208-16 (2007).
Gorden et al., Synthetic TLR agonists reveal functional differences between human TLR7 and TLR8, *J. Immunol.*, 174:1259-68 (2005).
Green et al., Mitochondria and apoptosis, *Science*, 281(5381):1309-12 (1998).
Griffiths et al., Studies toward Lipid A: Synthesis of differentially protected disaccharide fragments, *J. Org. Chem.*, 62(11):3654-8 (1997).
Gutsmann et al., Lipopolysaccharide-binding protein-mediated interaction of lipid A from different origin with phospholipid membranes, *Phys. Chem.*, 2:4521-8 (2000).
Hajjar et al., Human Toll-like receptor 4 recognizes host-specific LPS modifications, *Nat. Immunol.*, 3(4):354-9 (2002).
Hampton et al., Macrophage catabolism of lipid A is regulated by endotoxin stimulation, *J. Biol. Chem.*, 266(29):19499-509 (1991).
Harmey et al., Lipopolysaccharide-induced metastatic growth is associated with increased angiogenesis, vascular permeability and tumor cell invasion. *Int. J. Cancer*, 101: 415-22 (2002).
Hasegawa et al., Elevated promotion of prostacyclin production by synthetic lipid A analogs in aged human endothelial cells in culture, *Mech. Ageing Develop.*, 78:155-62 (1995).
Hawkins et al., A novel class of endotoxin receptor agonists with simplified structure, toll-like receptor 4-dependent immunostimulatory action, and adjuvant activity, *J. Pharmacol. Exper. Therap.*, 300(2):655-61 (2002).
Helander et al., Chemical structure of the lipopolysaccharide of *Haemophilus influenzae* strain 1-69 Rd–/b+, *Eur. J. Biochem.*, 177:483-92 (1988).
Hemmi et al., Small anti-viral compounds activate immune cells via the TLR7 MyD88-dependent signaling pathway, *Nat. Immunol.*, 3(2):196-200 (2002).
Hilgers et al., Synergistic effects of synthetic adjuvants on the humoral immune response, *Mt. Archs. Allergy Appl. Immunol.*, 79(4):392-6 (1986).
Hilgers et al., Synthetic sulpholipopolysaccharides: novel adjuvants for humoral immune responses, *Immunology*, 60(1):141-6 (1987).
Homma et al., Structural Requirements of Lipid A Responsible for the Functions: A study with chemically synthesized lipid A and its analogues, *J. Biochem.*, 98(2):395-406 (1985).
Horsmans et al., Isatoribine, an agonist of TLR7, reduces plasma virus concentration in chronic Hepatitis C infection, *Hepatol.*, 42(3):724-31 (2005).
Hubert et al., STEAP: A prostate-specific cell-surface antigen highly expressed in human prostate tumors, *Prot. Natl. Acad. Sci. USA*, 96(25):14523-8 (1999).
Imoto et al., Chemical synthesis of phosphorylated tetraacyl disaccharide corresponding to a biosynthetic precursor of Lipid A, *Tetrahedron Lett.*, 25(25):2667-70 (1984).
Imoto et al., Total synthesis of *Escherichia coli* lipid A, *Tetrahedron Lett.*, 26(12):1545-8 (1985).
Imoto et al., Total synthesis of *Escherichia coli* lipid A, the endotoxically active principle of the cell-surface lipopolysaccharide, *Bull. Chem. Soc. JP*, 60:2205-14 (1987).
Imoto et al., Total Synthesis of Lipid A, Active Principle of Bacterial Endotoxin, *Proc. Japan Acad.*, 60(B):285-8 (1984).
Invoices for the sale of PHAD™ from Avanti Polar Lipids, Inc. to AC Immune SA.
Isambert et al., Phase I study of OM-174, a lipid A analogue, with assessment of immunological response, in patients with refractory solid tumors. *BMC Cancer*, 13: 172-83 (2013).
Ishida et al., Regression of line-10 hepatocellular carcinoma by a less toxic cord factor analogue combined with L18-MDP or synthetic lipid A analogues. *Vaccine*, 6: 440-4 (1988).
Jacobson et al, Epidemiology and estimated population burden of selected autoimmune diseases in the United States, *Clin. Immunol. Immunopathol.*, 84(3):223-43 (1997).
Jiang et al., Lipid A structures containing novel lipid moieties: Synthesis and adjuvant properties, *Bioorg. Med. Chem. Lett.*, 12:2193-96 (2002).
Jiang et al., Monophosphoryl lipid A analogues with varying 3-0-substitution: synthesis and potent adjuvant activity, *Carbohydrate Research*, 342(6):784-96 (2007).
Jiang et al., Novel lipid A mimetics derived from pentaerythritol: synthesis and their potent agonistic activity, *Tetrahedron*, 58:8833-42 (2002).
Johansen et al., Toll-like receptor ligands as adjuvants in allergen-specific immunotherapy, *Clin. Exp. Allerg.*, 35(12):1591-8 (2005).
Johnson et al., 3-0-Desacyl monophosphoryl Lipid A derivatives: Synthesis and immunostimulant activities, *J. Med. Chem.*, 42(22):4640-9 (1999).
Johnson et al., A comparison of the immunomodulating properties of two forms of monophosphoryl lipid A Analogues, *J. Immunother.*, 10:398-404 (1991).
Johnson et al., Chemical synthesis of the major constituents of *Salmonella minnesota* moniphosphoryl lipid A, *J. Carb. Chem.*, 7(9):1421-6 (1998).
Johnson et al., TLR4 agonists as vaccine adjuvants, *Vacc. Adjuv. Deliv. Syst.*, 131-56 (2007).
Johnson, Molecular adjuvants and immunomodulators: New approaches to immunization, *Clin. Microbiol. Rev.*, 7(3):277-89 (1994).
Jurgens et al., Interaction of hemoglobin with enterobacterial lipopolysaccharide and lipid A, *Eur. J. Biochem.*, 268:4233-42 (2001).
Kaisho et al., Pleiotropic function of toll-like receptors, *Microbes Infect.*, 6(15):1388-94 (2004).
Kanegasaki et al., Biological activities of analogues of lipid A based chemically on the revised structural model, *Eur. J. Biochem.*, 143(2):237-42 (1984).
Kanegasaki et al., Structure-activity relationship of lipid A: comparison of biological activities of natural and synthetic lipid A's with different fatty acid compositions, *J. Biochem.*, 99(4):1203-10 (1986).
Kanzler et al., Therapeutic targeting of innate immunity with Toll-like receptor agonists and antagonists, *Nature Medicine*, 13(5):552-9 (2007).
Kasai et al., Immunochemistry of lipid A, *Adv. Exp. Med. Biol.*, 256:71-9 (1990).
Kasai et al., In Vitro antigenic reactivity of synthetic lipid A analogues as determined by monoclonal and conventional antibodies, *Biochem. Biophys. Res. Commun.*, 128(2):607-12 (1985).
Kasai et al., Structure-activity relationships of endotoxic lipid A containing 2,3-diamino-2,3-dideoxy-D-glucose, in Cellular and

(56) References Cited

OTHER PUBLICATIONS

Molecular Aspects of Endotoxin Reactions: Proceeding of the 1st congress of the international endotoxin society, Elsevier Science Publishers B.V. (Biomedical Division), San Diego, May 9-12, 121-8 (1990).
Kawahara et al., Modification of the structure and activity of lipid A in *Yersinia pestis* lipopolysaccharide by growth temperature, *Infect. Immunity*, 70(8):4092-8 (2002).
Kelly et al., TLR-4 Signaling promotes tumor growth and paclitaxel chemoresistance in ovarian cancer. *Cancer Res.* 66: 3859-68 (2006).
Kensil et al., Separation and characterization of saponins with adjuvant activity from Quillaja Saponaria molina cortex, *J. Immunology*, 46(2):431-7 (1991).
Kensil, Saponins as vaccine adjuvants, *Crit. Rev. Ther. Drug Carrier Syst.*, 13(1-2):1-55 (1996).
Kersten et al., Liposomes and ISCOMs, *Vaccine*, 21:915-20 (2003).
Kim et al., Crystal Structure of the TLR4-MD-2 complex with bound endotoxin antagonist eritoran, *Cell*, 130:906-17 (2007).
Kiso et al., Synthesis of the Optically Active 4-0-phosphono-d-glucosamine derivatives related to the nonreducing-sugar subunit of bacterial lipid A, *Carbohyd. Res.*, 162:127-40 (1987).
Knirel et al., Conserved and variable structural features in the lipopolysaccharide of *Pseudomonas aeruginosa*, *J. Endotox. Res.*, 12(6):324-36 (2006).
Kolls et al., Prolonged and effective blockade of tumor necrosis factor activity through adenovirus-mediated gene transfer, *Proc. Natl. Acad. Sci. USA*, 91:215-9 (1994).
Kotani et al., Immunobiological activities of synthetic lipid A analogs with low endotoxicity, *Infect. Immunity*, 54(3): 673-8 (1986).
Kotani et al., Low endotoxic activities of synthetic *Salmonella*-type lipid A with an additional acyloxyacyl Group on the 2-Amino group of beta(1-6)glucosamine disaccharide 1,4'-bisphosphate, *Infect. Immunity*, 52(3):872-84 (1986).
Kotani et al., Structural requirements of lipid A. endotoxicity and other biological activities—An overview, *Adv. Exp. Med. Biol.*, 256:13-43 (1990).
Kotani et al., Synthetic lipid A with endotoxic and related biological activities comparable to those of a natural lipid a from an *Escherichia coli* re-mutant, *Infect. Immunity*, 49(1):225-37 (1985).
Kukuoka et al., Structural characterization of lipid A component of *Erwinia carotovora* lipopolysaccharide. *Arch. Microbiol.* 157: 311-8 (1992).
Kumazawa et al., Importance of fatty acid substituents of chemically synthesized lipid A-subunit analogs in the expression of immunopharmacological activity, *Infect. Immunity*, 56(1):149-55 (1988).
Kusumoto et al., Structural basis for endotoxic and antagonistic activities: investigation with novel synthetic lipid a analogs, *J. Endotox. Res.*, 9(6):361-6 (2003).
Kusumoto et al., Synthesis of endotoxic principle of bacterial lipopolysaccharide and its recognition by the innate immune systems of hosts, *Chem. Record*, 6:333-43 (2006).
Lacaille-Dubois et al., A review of the biological and pharmacological activities of saponins, *Phytomedicine*, 2(4):363-86 (1996).
Lee et al., Activation of anti-Hepatitis C virus responses via toll-like receptor 7, *Proc. Nat. Acad. Sci. USA*, 103(6):1828-33 (2006).
Letter from the Opponent, Opposition against EP 2068918, Opposition by Avanti Polar Lipids, Inc. dated Mar. 4, 2014.
Letter from Thomas G. Peterson to Steven G. Reed, Ph.D. dated Mar. 4, 2011.
Li et al., Assessment of recombinant adenoviral vectors for hepatic gene therapy, *Hum. Gene Ther.*, 4(4):403-9 (1993).
Lien et al., A novel synthetic acyclic lipid A-like agonist activates cells via the lipopolysaccharide/Toll-like Receptor 4 signaling pathway, *J. Biol. Chem.*, 276(3):1873-80 (2001).
Lien et al., Adjuvants and their signaling pathways: Beyond TLRs, *Nat. Immunol.*, 4(12):1162-4 (2003).
Life Sciences Discovery Fund Announces Grants to Commercialize Health-Related Products and Services, Jun. 27, 2013.
Lin et al., Implication of toll-like receptor and tumor necrosis factor alpha signaling in septic shock, *Shock*, 24(3):206-9 (2005).
Liu et al., A divergent synthesis of lipid A and its chemically stable unnatural analogues, *Bull. Chem. Soc. Jpn.*, 72:1377-85 (1999).
Liu et al., Enzymatic preparation of (S)-3-Hydroxytetradecanoic acid and synthesis of unnatural analogues of lipid A containing the (S)-Acid, *Bull. Chem. Soc. Jpn.*, 70:1441-50 (1997).
Liu, Vaccine developments, *Nat. Med.*, 4(5):515-9 (1998).
Loppnow et al., Lipid A, The immunostimulatory principle of lipopolysaccharides?, *Adv. Exp. Med. Biol.*, 156:561-6 (1990).
Lu et al., A Novel Gene (PLU-1) containing highly conserved putative dna/chromatin binding motifs is specifically up-regulated in breast cancer, *J. Biol. Chem.*, 274(22):15633-45 (1999).
Luster, The role of chemokines in linking innate and adaptive immunity, *Curr. Opin. Immunol.*, 14(1):129-35 (2002).
Maeda et al., Adjuvant activities of synthetic lipid A subunit analogues and its conjugates with muramyl dipeptide derivatives, *Vaccine*, 7(3):275-81 (1989).
Mai et al., Should a toll-like receptor 4 (TLR-4) agonist or antagonist be designed to treat cancer? TLR-4: Its expression and effects in the ten most common cancers. *OncoTargets Ther.* 6: 1573-87 (2013).
Malakoff, Aluminum is put on trial as a vaccine booster, *Science*, 288(5470):1323-4 (2000).
Masoud et al., Investigation of the structure of lipid A from *Actinobacillus actinomycetemcomitans* strain Y4 and human clinical isolate PO 1021-7, *Eur. J. Biochem.*, 200:775-9 (1991).
Mata-Haro et al., The vaccine adjuvant monophosphoryl lipid A as a TRIF-biased agonist of TLR4, *Science*, 316:1628-2 (2007).
McCluskie et al., CpG DNA is a potent enhancer of systemic and mucosal immune responses against hepatitis B surface antigen with intranasal administration to Mice, *J. Immunol.*, 161(9):4463-6 (1998).
Medzhitov et al., Innate immunity: Impact on the adaptive immune response, *Curr. Opin. Immunol.*, 9(1):4-9 (1997).
Medzhitov, Toll-like receptors and innate immunity, *Nat. Rev. Immunol.*, 1(2):135-45 (2001).
Melaugh et al., Partial characterization of the major lipooligosaccharide from a strain of *Haemophilus ducreyi*, the causative agent of chancroid, a genital ulcer disease, *J Biol. Chem.*, 267:13434-9 (1992).
Merck Index Online (SM), CAS Registry No. 11024-24-1, Digitonin, 2005.
Merck Index Online (SM), CAS Registry No. 111-02-4, Squalene, 2005.
Merck Index Online (SM), CAS Registry No. 6805-41-0, Escin, 2005.
Mikhail et al., Structural characterization of lipid A from nontypeable and type f *Haemophilus influenzae*: Variability of fatty acid substitution, *Analytical Biochem.*, 340:303-16 (2005).
Minutes of the MDR1 Teleconference, Jul. 26, 2005.
Mitchell et al., Expression of the pneumolysin gene in *Escherichia coli*: Rapid purification and biological properties, *Biochem. Biophys. Acta*, 1007:67-72 (1989).
Molavi et al., Immunomodulatory and anticancer effects of intratumoral co-delivery of synthetic lipid A adjuvant and STAT3 inhibitor, JSI-124, *Immunopharmacol. Immunotoxicol.* 31(2): 214-21 (2009).
Moran, Biological and serological characterization of *Campylobacter jejuni* lipopolysaccharides with deviating core and lipid A structures, *FEMS Immunol. and Med. Microbiol.*, 11:121-30 (1995).
Mueller et al., Aggregates are the biologically active units of endotoxin, *J. Biol.Chem.*, 279(25):26307-313 (2004).
Muotiala, et al., Low biological activity of *Helicobacter pylori* lipopolysaccharide, *Infect. Immunity*, 60(4):1714-16 (1992).
Myers et al., A critical determinant of lipid A endotoxic activity. Cellular and molecular aspects of endotoxic reactions, 145-56 (1990).
Nakao et al., Surface-expressed TLR6 participates in the recognition of diacylated lipopeptide and peptidoglycan in human cells, *J. Immunol.*, 174:1566-73 (2005).
Nakatsuka et al., Enhancement of nonspecific resistance to bacterial infections and tumor regressions by treatment with synthetic lipid

(56) References Cited

OTHER PUBLICATIONS

A-subunit analogs. Critical role of N- and 3-O-linked acyl groups in 4-O-phophono-D-glucosamine derivatives. *Int. J. Immunopharmacol.* 11(4): 349-58 (1989)—Abstract only.

Nakatsuka et al., Inhibition in mice of experimental metastasis of B16 melanoma by the synthetic lipid A-subunit analogue GLA-60, *Int. J. Immunopharmacol.* 13(1): 11-19 (1991).

Nelson et al., Molecular cloning and characterization of prostase, an androgen-regulated serine protease with prostate-restricted expression, *Proc. Natl. Acad. Sci. USA*, 96(6):3114-9 (1999).

Notice of Opposition Against European Patent No. 2 068 912-B1 (European Application No. 07 87 5082.5), Vaccine Composition Containing Synthetic Adjuvant, 36 pages, dated Feb. 1, 2013.

Oblak et al., Toll-like receptor 4 activation in cancer progression and therapy. *Clin. Dev. Immunol.* 2011: 609579 (2011).

Pance et al., Antitumoral effects of lipid A: Preclinical and clinical studies, *J. Investig. Med.* 50(3): 173-8 (2002).

PCT Application No. PCT/US2007/021017, International Filing Date Sep. 26, 2007, International Search Report and Written Opinion mailed Oct. 17, 2008.

PCT Application No. PCT/US2009/045033, International Filing Date May 22, 2009, International Search Report and Written Opinion mailed Mar. 9, 2010.

PCT Application No. PCT/US2010/37466, International Filing Date Jun. 4, 2010, International Search Report and Written Opinion mailed Aug. 25, 2010.

Persing et al., Taking Toll: Lipid A Mimetics as Adjuvants and Immunomodulators, *Trends in Microbiology*, 10(10):S32-7 (2002).

PHAD™ advertisement, *J. Biol. Chem.*, 282 (2007).

Piekarz et al., Epigenetic modifiers: Basic understanding and clinical development. *Clin. Cancer Res.* 15: 3918-26 (2009).

Qureshi et al., Complete structural determination of lipopolysaccharide obtained from deep rough mutant of *Escherichia coli*, *J. Biol. Chem.*, 263:11971-6 (1988).

Qureshi et al., Monophosphoryl lipid A obtained from lipopolysaccharides of *Salmonella minnesota* R595, *J. Biol. Chem.*, 260(9):5271-8 (1985).

Qureshi et al., Position of ester groups in the lipid A backbone of lipopolysaccharides obtained from *Salmonella typhimurium*, *J. Biol. Chem.*, 258(21):12947-51 (1983).

Qureshi et al., Purification and structural determination of nontoxic lipid A obtained from the lipopolysaccharide of *Salmonella typhimurium*, *J. Biol. Chem.*, 257(19):11808-15 (1982).

Raetz et al., Kdo2-lipid A of *Escherichia coli*, a defined endotoxin that activates macrophages via TLR-4, *J. Lipid Res.*, 47:1097-111 (2006).

Reed et al., An improved serodiagnostic procedure for visceral leishmaniasis, *Am. J. Trop. Med. Hyg.*, 43(6):632-9 (1990).

Reed et al., New horizons in adjuvants for vaccine development, Trends Immunol., 30(1):23-32 (2009).

Reisser et al., Mechanisms of the antitumoral effect of lipid A, *BioEssays*, 24: 284-9 (2002).

Reiter et al., Prostate stem cell antigen: A cell surface marker overexpressed in prostate cancer, *Proc. Nat. Acad. Sci. USA*, 95(4):1735-40 (1998).

Ribi et al., Beneficial modification of the endotoxin molecule, *J. Biol. Resp. Modifiers*,3:1-9 (1984).

Richards et al., Immunogenicity of liposomal malaria sporozoite antigen in monkeys: Adjuvant effects of aluminum hydroxide and non-pyrogenic liposomal lipid A, *Vaccine*, 7:506-12 (1989).

Rietschel et al., Bacterial endotoxin: molecular relationships of structure to activity and function, *FASEB J.*, 8:217-25 (1994).

Rietschel et al., Endotoxic properties of synthetic pentaacyl lipid A precursor lb and a structural isomer, *Eur. J. Biochem.*, 169:27-31 (1987).

Rietschel et al., Lipid A, the endotoxic center of bacterial lipopolysaccharides: Relation of chemical structure to biological activity, *Progr. Clin. Biol. Res.*, 231: 25-53 (1987).

Rietschel et al., The chemical structure of bacterial endotoxin in relation to bioactivity, *Immunobiology*, 187:169-90 (1993).

Robbins et al., Human tumor antigens recognized by T-Cells, *Curr. Opin. Immunol.*, 8(5):628-36 (1996).

Rothenberg et al., Stimulation of rabbit synoviocyte prostaglandin E2 synthesis by lipopolysaccharides and their subunit structures, *Arthritis and Rheumatism*, 31(2): 238-47 (1988).

Rubins et al., Pneumolysin in pneumococcal adherence and colonization, *Microb. Pathog.*, 25(6):337-42 (1998).

Rudbach et al., Ribi Adjuvants: Chemistry, biology and utility in vaccines for human and veterinary medicine, theory and practical application of adjuvants, 13:287-313 (1995).

Saiki et al., Inhibition of tumor-induced angiogenesis by the administration of recombinant interferon-gamma followed by a synthetic lipid-A subunit analogue (GLA-60), *Int. J. Cancer*, 51(4): 641-5 (1992)—Abstract only.

Salem et al., The adjuvant effects of the toll-like receptor 3 ligand polyinosinic-cytidylic acid poly (I:C) on antigen-specific CD8+ T cell responses are partially dependent on NK cells with the induction of a beneficial cytokine milieu, *Vaccine*, 24(24):5119-32 (2006).

Salkowski et al., Lipopolysaccharide and monophosphoryl lipid A differentially regulate interleukin-12, Gamma interferon, and interleukin-10 mRNA production in murine macrophages, *Infect. Immunity*, 65(8):3239-47 (1997).

Salomon et al., Cripto: A novel epidermal growth factor (EGF)-related peptide in mammary gland development and Neoplasia, *BioEssays*, 21(1):61-70 (1999).

Schirmbeck et al., Antigenic epitopes fused to cationic peptide bound to oligonucleotides facilitate toll-like receptor 9-Dependent, but CD4+ T cell help-independent priming of CD8+ T cells, *J. Immunol.*, 171(10):5198-207 (2003).

Schmidt et al., Cytokine and Ig-production by CG-containing sequences with phosphorodiester backbone and dumbbell shape, *Allergy*, 61(1):56-63 (2006).

Schnur et al., Leishmanial serotypes as distinguished by the gel diffusion of factors excreted in vitro and in vivo, *Isrl. J. Med. Sci.*, 8(7):932-42 (1972).

Schromm et al., Biological activities of lipopolysaccharides are determined by the shape of their lipid A portion, *Eur. J. Biochem.*, 267:2008-13 (2000).

Second Declaration of Steven Reed, Ph.D. with Appendices A and B, executed on Apr. 30, 2012, filed in U.S. Appl. No. 11/862,122.

Senaldi et al., Serological diagnosis of visceral leishmaniasis by a dot-enzyme immunoassay for the detection of a leishmania donovani-related circulating antigen, *J. Immunol. Methods*, 193(1):9-15 (1996).

Seong et al., Hydrophobicity: an ancient damage-associated molecular pattern that initiates innate immune responses, *Nat. Rev. Immunol.*, 4:469-78 (2004).

Sethi et al., Bacterial infection in Chronic Obstructive Pulmonary Disease in 2000: A State-of-the-Art Review, *Clin. Microbiol. Rev.*, 14(2):336-63 (2001).

Seydel et al., Intrinsic conformation of lipid A is responsible for agonistic and antagonistic activity, *Eur. J. Biochem.*, 267:3032-9 (2000).

Seydel et al., Physicochemical characterization of carboxymethyl lipid A derivatives in relation to biological activity, *FEBS J.*, 272:327-40 (2005).

Seydel et al., Supramolecular structure of lipopolysaccharide and free lipid A under physiological conditions as determined by synchrotron small-angle X-ray diffraction, *Eur. J. Biochem.*, 186:325-32 (1989).

Simon, CRC Desk Reference for Allergy and Asthma, CRC Press LLC, 20-3 (2000).

Soboll et al., Expression of Toll-Like Receptors (TLR) and responsiveness to TLR agonists by polarized mouse uterine epithelial cells in culture, *Biol. Reprod.*, 75(1):131-9 (2006).

Srivastava et al., Costimulatory SA-4-1BBL and monophophoryl lipid A as novel adjuvant system for the development of cancer vaccines with robust therapeutic efficacy, *Cancer Res.* 1(8): Suppl. 1 (2011)—Abstract 765.

Steers et al., Modulation of immunoproteasome subunits by liposomal lipid A, *Vaccine*, 26:2849-59 (2008).

(56) References Cited

OTHER PUBLICATIONS

Stone et al., Nanoparticles-delivered multimeric soluble CD4OL DNA combined with toll-like receptor agonists as a treatment for melanoma, *PLoS One,* 4(10): e7334 (2009).
Stover et al., Structure activity relationship of synthetic Toll-Like Receptor 4 agonists, *J. Biol. Chem.,* 279(6):4440-9 (2004).
Takada et al., Immunopharmacological Activities of a Synthetic Counterpart of a Biosynthetic Lipid A precursor molecule and of its analogs, *Infect. Immunity,* 48(1):219-27 (1985).
Takada et al., Structural requirements of lipid A for endotoxicity and other biological activities, *CRC Crit. Rev. Microbiol.,* 16(6):477-523 (1989).
Takada et al., Structural requirements of lipid A species in activation of clotting enzymes from the horseshoe crab, and the human complement cascade, *Eur. J. Biochem.,* 175:573-80 (1988).
Takayama et al., Adjuvant Activity of non-ionic block copolymers V. Modulation of antibody isotype by lipopolysaccharides, lipid A and precursors, *Vaccine,* 9:257-65 (1991).
Takayama et al., Complete structure of lipid a obtained from the lipopolysaccharides of the heptoseless mutant of *Salmonella typhimurium, J. Biol. Chem.,* 258(21):12801-3 (1983).
Takayama et al., Influence of fine structure of lipid A in *Limulus* amebocyte lysate clotting and toxic activities, *Infect. Immun.,* 45(2):350-55 (1984).
Takayama et al., Isolation of a nontoxic lipid A fraction containing tumor regression activity. *Cancer Res.* 41: 2654-7 (1981).
Takeda et al., Toll-like receptors in innate immunity, *Int. Immunol.* 17(1):1-14 (2005).
Takeda et al., Toll-like receptors, *Ann. Rev. Immunol.,* 21:335-76 (2003).
Tamai et al., Cell activation by monosaccharide lipid A analogues utilizing Toll-like receptor 4, *Immunology,* 110:66-72 (2003).
Tanamoto, Dissociation of endotoxic activities in a chemically synthesized lipid a precursor after acetylation, *Infect. Immunity,* 63(2):690-2 (1995).
Tanamoto, *Salmonella*-type heptaacylated Lipid A is inactive and acts as an antagonist of lipopolysaccharide action on human line cells, *J. Immunol.,* 164:3149-56 (2000).
Teghanemt et al., Molecular basis of reduced potency of underacylated endotoxins, *J. Immun.,* 175:4669-76 (2005).
Therisod et al., *Helicobacter mustelae* lipid A structure differs from that of *Helicobacter pylori, FEBS Lett,.* 499:1-5 (2001).
Thompson et al., The low-toxicity versions of LPS, MPL® adjuvant and RC529, are efficient djuvants for CD4 T cells, *J. Leukoc. Biol.,* 78:1273-80 (2005).
Trent et al., Diversity of endotoxin and its impact on pathogenesis, *J. Endotox. Res.,* 12(4):205-23 (2006).
Triantafilou et al., Combinational clustering of receptors following stimulation by bacterial products determines lipopolysaccharide responses, *Biochem. J.,* 381 :527-36 (2004).
Triozzi et al., Effects of a beta-human chorionic gonadotropin subunit immunogen administered in aqueous solution with a novel nonionic block copolymer adjuvant in patients with advanced cancer, *Clin. Cancer Res.,* 3(12 Pt 1):2355-62 (1997).
Tsan et al., Cytokine function of heat shock proteins, *Am. J. Physiol. Cell Physiol.,* 286(4):C739-44 (2004).
Tsan et al., Endogenous ligands of Toll-Like Receptors, J. Leukoc. Biol., 76(3):514-9 (2004).
U.S. Appl. No. 11/862,122, filed Sep. 26, 2007, Final Office Action mailed Feb. 1, 2010.
U.S. Appl. No. 11/862,122, filed Sep. 26, 2007, Office Action mailed Jul. 28, 2009.
U.S. Appl. No. 11/862,122, filed Sep. 26, 2007, Office Action mailed May 5, 2011.
U.S. Appl. No. 12/351,710, filed Jan. 9, 2009, Office Action mailed Dec. 13, 2010.
Ukei et al., Adjuvant and antitumour activities of synthetic lipid A analogues, *Vaccine,* 4:21-24 (1986).
Ulrich et al., Topics in vaccine adjuvant research, Chapter 12, The Adjuvant Activity of Monophosphoryl Lipid A, 133-43 (1991).

Van De Voort et al., Intratumoral delivery of low doses of anti-CD40 mAb combined with monophosphoryl lipid A induces local and systemic antitumor effects in immunocompetent and T cell-deficient mice. *J. Immunother.* 36(1): 29-40 (2013).
Van den Eynde et al., Tumor antigens recognized by t-lymphocytes, *Mt. J. Clin. Lab. Res.,* 27:81-6 (1997).
Velasco et al., Toll-Like Receptor 4 or 2 agonists decrease allergic inflammation, *Amer. J. Resp. Cell Molec. Biol.,* 32:218-24 (2005).
Vincent et al., Long-term correction of mouse dystrophic degeneration by adenovirus-mediated transfer of a minidystrophin gene, *Nat. Genet.,* 5(2):130-4 (1993).
Vollmer et al., Immunopharmacology of CpG oligodeoxynucleotides and ribavirin, *Antimicrob. Agents Chemother.,* 48(6):2314-7 (2004).
Vollmer, Progress in drug development of immunostimulatory CpG oligodeoxynucleotide ligands for TLR9, *Exp. Opin. Biolog. Ther.,* 5(5):673-82 (2005).
Vosika et al., Phase-I study of intravenous modified lipid A, *Cancer Immunol. Immunother.* 18(2): 107-12 (1984)—Abstract only.
Wang et al., Inhibition of endotoxin-induced interleukin-6 production by synthetic lipid A partial structure in human peripheral blood mononuclear cells, *Infect. Immun.,* 59(12):4655-64 (1991).
Wang et al., pH-sensitive Immunoliposomes mediate target-cell-specific delivery and controlled expression of a foreign gene in mouse, *Proc. Natl. Acad. Sci. USA,* 84:7851-5 (1987).
Wasylyk et al., The Ets Family of Transcription Factors, *Eur. J. Biochem.,* 211(1-2):7-18 (1993).
Webpage from List Biological Laboratories, Inc. showing the 'order products online' page for lipopolysaccharides.
Weeratna et al., TLR Agonists as Vaccine Adjuvants: Comparison of CpG ODN and Resiquimod (R-848), *Vaccine,* 23(45):5263-70 (2005).
Weihrauch et al., Phase I/II Combined chemoimmunotherapy with carcinoembryonic antigen-derived HLA-A2-restricted CAP-1 peptide and irinotecan, 5-Fluorouracil, and leucovorin in patients with primary metastatic colorectal cancer, *Clin. Cancer Res.,* 11(16):5993-6001 (2005).
Wheeler et al., Allergy vaccines—new approaches to an old concept, *Exp. Opin. Biol.Ther.,* 4(9):1473-81 (2004).
Wu et al., Targeting genes: Delivery and persistent expression of a foreign gene driven by mammalian regulatory elements in vivo, *J. Biol. Chem.,* 264(29):16985-87 (1989).
Xiong et al., Inhibition of interleukin-12 p40 Transcription and NF-kB activation by nitric oxide in murine macrophages and dendritic cells, *J. Biol. Chem.,* 279(11):10776-83 (2004).
Yang et al., The immunogenicity-enhancing effect of emulsion vaccine adjuvants is independent of the dispersion type and antigen release rate—a revisit of the role of the hydrophile-lipophile balance (HLB) value, *Vaccine,* 23:2665-75 (2005).
Yasuda et al., Biological activity of chemically synthesized analogues of lipid A, *Euro. J. Biochem.,* 124(2):405-7 (1982).
Yasuda et al., Further study of biological activities of chemically synthesized analogues of lipid A in artificial membrane vesicles, *Eur. J. Biochem.,* 140(2):245-8 (1984).
Yeh et al., Improving protein delivery from microparticles using blends of Poly(DL Lactide Co-Glycolide) and Poly(Ethylene Oxide)-Poly(Propylene Oxide) Copolymers, Pharm. Res., 13(11):1693-8 (1996).
Yoshida et al., Endotoxic properties of chemically synthesized lipid A analogs, *Microbiol. Immunol.,* 33(10):797-810 (1989).
Yoshida et al., Monophosphoryl Lipid A induces pharmacologic 'preconditioning' in rabbit hearts without concomitant expression of 70-kDa heat shock protein, *Molec. Cell. Biochem.,* 156:1-8 (1996).
Yoshikawa et al., Bioactive saponins and glycosides. III. Horse Chestnut. (1): The structures, inhibitory effects on ethanol absorbtion, and hypoglycemic activity of escins Ia, Ib, IIa, IIb, and IIIa from the seeds of aesculus Hippocastanum L., *Chem. Pharm. Bull.,* 4(8):1454-64 (1996).
Zahringer et al., Molecular structure of lipid A, the endotoxic center of bacterial lipopolysaccharides, *Adv. Carbohydrate Chem. Biochem.,* 50:211-76 (1994).

(56) References Cited

OTHER PUBLICATIONS

Zijlstra et al., The direct agglutination test for diagnosis of visceral leishmaniasis under field conditions in sudan: comparison of aqueous and freeze-dried antigens, *Trans. R. Soc. Trop. Med. Hyg.,* 91(6):671-3 (1997).

Akira et al., Toll-like receptors: critical proteins linking innate and acquired immunity. *Nat. Immunol.* 2: 675-80 (2001).

Beutler et al., Cachectin and tumour necrosis factor as two sides of the same biological coin. *Nature,* 320: 584-8 (1986).

Beutler, Innate immunity: an overview. *Mol. Immunol.* 40: 845-59 (2004).

Bevan, Helping the CD8(+) T-cell response. *Nat. Rev. Immunol.* 4: 595-602 (2004).

Buhtoiarov et al., CD40 ligation activates murine macrophages via an IFN-gamma-dependent mechanism resulting in tumor cell destruction in vitro. *J Immunol.* 174: 6013-22 (2005).

Chen et al., Oncology meets immunology: the cancer-immunity cycle. *Immunity,* 39: 1-10 (2013).

Dabbagh et al., Toll-like receptors and T-helper-1/T-helper-2 responses. *Curr. Opin. Infect. Dis.* 16: 199-204 (2003).

Finlay et al., Can innate immunity be enhanced to treat microbial infections? *Nat. Rev. Microbiol.* 2: 497-504 (2004).

Iwasaki et al., Toll-like receptor control of the adaptive immune responses. *Nat. Immunol.* 5: 987-95 (2004).

Kriegler et al., a novel form of TNF/cachectin is a cell surface cytotoxic transmembrane protein: ramifications for the complex physiology of TNF. *Cell,* 53: 45-53 (1988).

Pardoll, The blockade of immune checkpoints in cancer immunotherapy. *Nature,* 12: 252-64 (2012).

Pasare et al., Toll-dependent control mechanisms of CD4 T cell activation. *Immunity,* 21: 733-41 (2004).

Pasare et al., Toll-like receptors and acquired immunity. *Seminars Immunol.* 16: 23-6 (2004).

Pittet et al., Nosocomial bloodstream infection in critically ill patients. Excess length of stay, extra costs, and attributable mortality. *J. Am. Med. Assoc.* 271: 1598-601 (1994).

Powell et al. (Eds.), Vaccine Design: The subunit and adjuvant approach, Chapter 21 Monophosphoryl Lipid A as an adjuvant: Past experiences and new directions by Ulrich et al. Plenum Press, New York (1995).

Rice et al., Therapeutic intervention and targets for sepsis. *Annu. Rev. Med.* 56: 225-48 (2005).

Smith et al., The active form of tumor necrosis factor is a trimer. *J. Biol. Chem.* 262: 6951-4 (1987).

Ulrich et al., Vaccine design: The subunit and adjuvant approach, Plenum Press, New York, Chapter 21, Monophosphoryl Lipi A as an Adjuvant, 495-524 (1995).

van Amersfoort et al., Receptors, mediators, and mechanisms involved in bacterial sepsis and septic shock. *J. Clin. Microbiol. Rev.* 16: 379-414 (2003).

\* cited by examiner

A

GLA MONOTHERAPY FOR USE IN CANCER TREATMENT

FIELD

The present disclosure relates generally to compositions and methods for treating cancer with a glucopyranosyl lipid A (GLA).

BACKGROUND

The innate immune system is an evolutionarily ancient system designed to detect the presence of microbial invaders and activate protective reactions (Beutler, Mol. Immunol. 2004, 40, 845-859). It responds rapidly to compounds that are integral parts of pathogens that are perceived as danger signals by the host. Recognition of these molecular patterns is mediated by sets of highly conserved receptors (van Amersfoort et al., J. Clin. Microbiol. Rev. 2003, 16, 379), whose activation results in acute inflammatory responses. These responses include the production of a diverse set of cytokines and chemokines, directing local attacks against the invading pathogen, and initiation of responses that activate and regulate the adaptive component of the immune system (Dabbagh and Lewis, Curr. Opin. Infect. Dis. 2003, 16, 199-204; Bevan, Nat. Rev. Immunol. 2004, 4, 595-602; Pasare and Medzhitov, Seminars Immunol. 2004, 16, 23-26; Finlay and Hancock, Nat. Rev. Microbiol. 2004, 2, 497-504; Akira et al., Nat. Immunol. 2001, 2, 675-680; Pasare and Medzhitov, Immunity 2004, 21, 733-741).

Evidence is emerging that innate immune responses can be exploited for therapeutic purposes such as the development of adjuvants for vaccines and the treatment of a wide range of diseases including asthma, infections, and cancer. An important concern of such therapies is, however, that over-activation of innate immunity may lead to the clinical symptoms of septic shock (Pittet et al., J. Am. Med. Assoc. 1994, 271, 1598-1601; Rice and Bernard, Anna. Rev. Med. 2005, 56, 225-248).

It has long been a goal in cancer immunology to enhance immune-mediated antitumor activity, to achieve tumor regression and improve cancer treatment options. Clearly there is a need for improved compositions and methods for enhancing anti-tumor immune responses for use as cancer treatments. The present invention provides this and other related advantages.

SUMMARY OF THE INVENTION

One aspect of the present invention provides a method of treating a mammal who suffers from cancer, comprising administering an effective amount of a composition comprising GLA, said composition comprising:
(a) GLA of the formula:

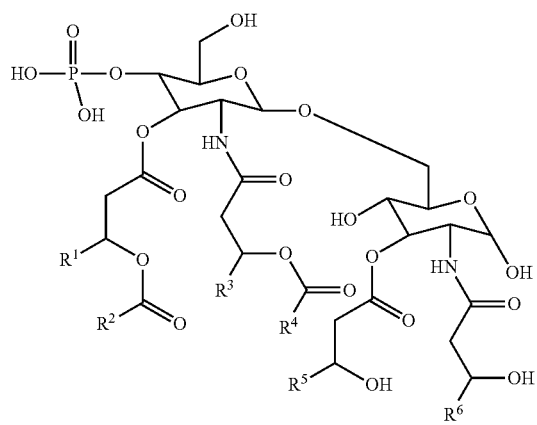

wherein: $R^1$, $R^3$, $R^5$ and $R^6$ are $C_{11}$-$C_{20}$ alkyl; and $R^2$ and $R^4$ are $C_{12}$-$C_{20}$ alkyl; and
(b) a pharmaceutically acceptable carrier or excipient; wherein the composition does not comprise antigen. In one embodiments of the methods described herein, $R^1$, $R^3$, $R^5$ and $R^6$ are undecyl and $R^2$ and $R^4$ are tridecyl. In another embodiment of the methods described herein, the mammal is human. In yet a further embodiment, the composition is an aqueous formulation, and in certain embodiments, the composition is in the form of an oil-in-water emulsion, a water-in-oil emulsion, liposome, micellar formulation, or a microparticle.

In certain embodiments of the methods described herein, the cancer comprises a solid tumor, and may be a carcinoma, a sarcoma or a lymphoma. In another embodiment, the solid tumor is a primary solid tumor or may be a secondary solid tumor. The present methods may be used for the treatment of a variety of cancers, including but not limited to, melanoma, Merkel cell carcinoma, non-Hodgkin's lymphoma (NHL), lung cancer, cervical cancer, ovarian cancer, uterine cancer, breast cancer, liver cancer, gastric cancer, prostate cancer, colon cancer, kidney cancer, bladder cancer, brain cancer, and pancreatic cancer.

In certain embodiments, the composition is administered by subcutaneous, intradermal, intramuscular, intratumoral, or intravenous injection. In additional embodiments, the composition is administered intranasally or intrapulmonary.

In another embodiment of the methods described herein, the composition is administered in conjunction with one or more additional therapeutic agents or treatments. In this regard, in certain embodiments, the therapeutic agent is an anti-cancer agent. The additional therapeutic agents or treatments may be a chemotherapeutic agent, an immune checkpoint inhibitor, or an antibody that activates a co-stimulatory pathway, such as but not limited to anti-CD40 antibodies. Any of a number of therapeutic agents is contemplated for use herein, including, but not limited to, taxotere, carboplatin, trastuzumab, epirubicin, cyclophosphamide, carboplatin, cisplatin, docetaxel, doxorubicin, etoposide, 5-FU, gemcitabine, methotrexate, and paclitaxel. In certain embodiments, the one or more additional therapeutic treatments is radiation therapy.

DETAILED DESCRIPTION

Figure 1:
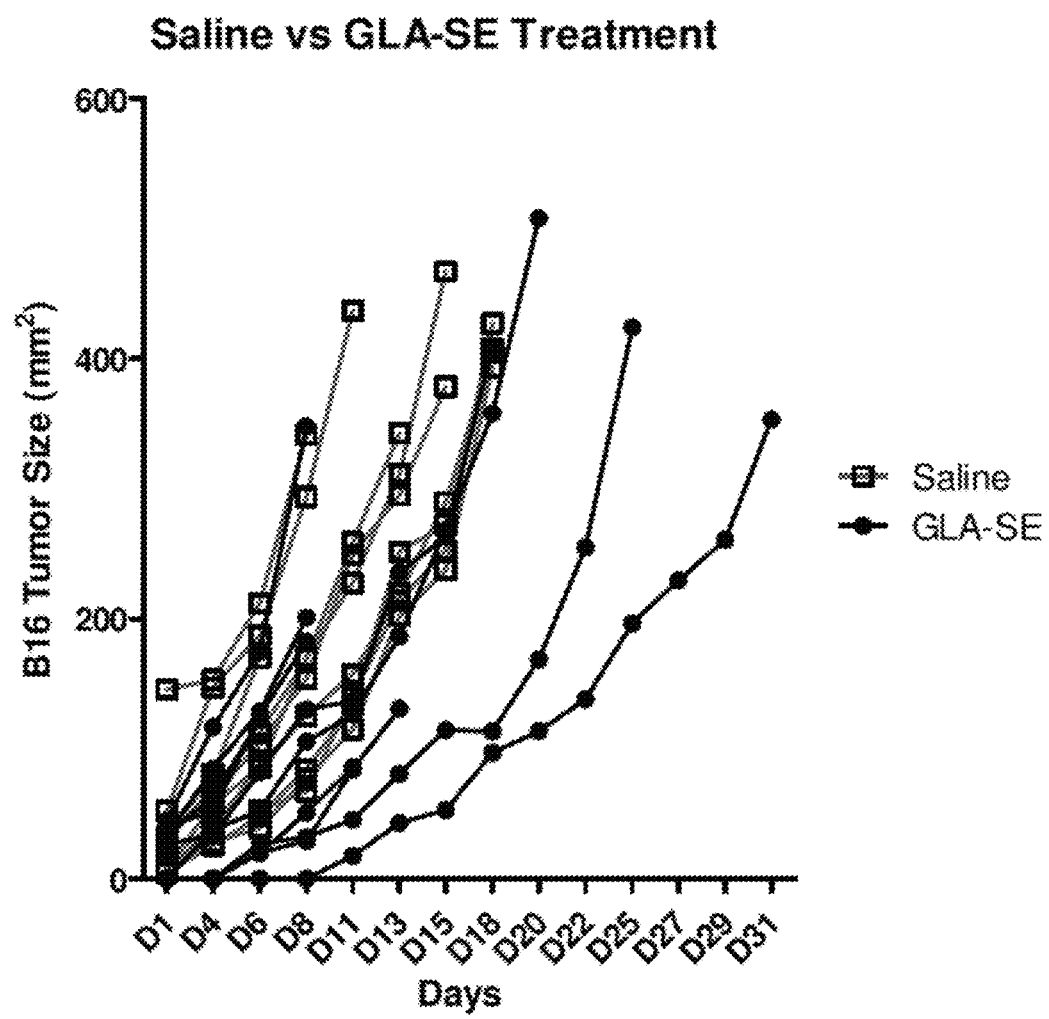
FIG. 1 is a graph of tumor size over time in mice administered saline or GLA following injection with B16 melanoma cells.

The present disclosure relates in part to the surprising observation that GLA administration alone, given after cancer has been established, resulted in an increase in survival in mice in a B16 melanoma mouse model. GLA has been used as a vaccine adjuvant to enhance immune responses to a variety of antigens. However, prior to the present application, GLA has not been used as a monotherapy for the treatment of cancer.

As used herein and in the appended claims, the singular forms "a," "and," and "the" include plural referents unless the context clearly dictates otherwise. Thus, for example, reference to "an antigen" includes a plurality of such antigens, and reference to "a cell" or "the cell" includes reference to one or more cells and equivalents thereof (e.g., plurality of cells) known to those skilled in the art, and so forth. Similarly, reference to "a compound" or "a composition" includes a plurality of such compounds or compositions, and refers to one or more compounds or compositions, respectively, unless the context clearly dictates otherwise. When steps of a method are described or claimed, and the steps are described as occurring in a particular order, the description of a first step occurring (or being performed) "prior to" (i.e., before) a second step has the same meaning if rewritten to state that the second step occurs (or is performed) "subsequent" to the first step. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

The methods and compositions herein apply to treatment of any mammal, including humans. Other mammals include small domesticated animals, particularly companion animals and pets, including but not limited to, mice, rats, hamsters, guinea-pigs, rabbits, cats, dogs, and primates. Mammals that may be treated include, for example, non-human primates (e.g., monkey, chimpanzee, gorilla, and the like), rodents (e.g., rats, mice, gerbils, hamsters, ferrets, rabbits), lagomorphs, swine (e.g., pig, miniature pig), equine, canine, feline, bovine, and other domestic, farm, and zoo animals. Subjects in need of the treatments described herein have been diagnosed with cancer, or may have signs of a hyperproliferative disorder that renders the subject at risk of developing cancer. Exemplary cancer conditions are described in further detail herein.

The GLA compounds suitable for use according to the present disclosure include any of the following. Without being bound by a theory of the invention, the GLA compounds described herein are believed to target TLR4. TLR4 is unique among the TLR family in that downstream signaling occurs via both the MyD88- and TRIF-dependent pathways. Collectively, these pathways stimulate DC maturation, antigen processing/presentation, T cell priming, and the production of cytokines (e.g., IL-12, IFNα/β, and TNFα) (see, e.g., Iwasaki et al., Nat. Immunol. 5:987 (2004)).

A glucopyranosyl lipid A (GLA) compound of formula (Ia):

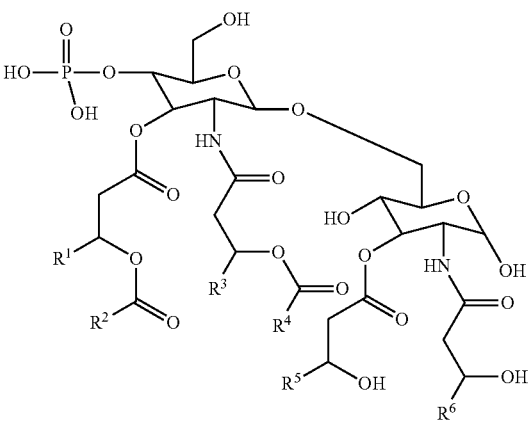

or a pharmaceutically acceptable salt thereof, where: R1, R3, R5 and R6 are C11-C20 alkyl; and R2 and R4 are C12-C20 alkyl; in a more specific embodiment, the GLA has the formula (Ia) set forth above wherein R1, R3, R5 and R6 are C11-14 alkyl; and R2 and R4 are C12-15 alkyl; in a further more specific embodiment, the GLA has the formula (Ia) set forth above wherein R1, R3, R5 and R6 are C11 alkyl, or undecyl; and R2 and R4 are C13 alkyl, or tridecyl;

or of formula (Ib):

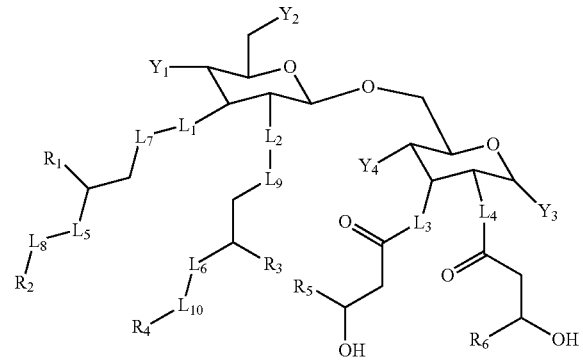

or a pharmaceutically acceptable salt thereof, wherein: L1, L2, L3, L4, L5 and L6 are the same or different and are independently selected from O, NH, and (CH2); L7, L8, L9 and L10 are the same or different, and at any occurrence may be either absent or C(=O); Y1 is an acid functional group; Y2 and Y3 are the same or different and are each independently selected from OH, SH, and an acid functional group; Y4 is OH or SH; R1, R3, R5 and R6 are the same or different and are each independently selected from the group of C8-C13 alkyl; and R2 and R4 are the same or different and are each independently selected from the group of C6-C11 alkyl.

A DSLP compound is a type of GLA that contains a disaccharide (DS) group formed by the joining together of two monosaccharide groups selected from glucose and amino substituted glucose, where the disaccharide is chemically bound to both a phosphate (P) group and to a plurality of lipid (L) groups. More specifically, the disaccharide may be visualized as being formed from two monosaccharide units, each having six carbons. In the disaccharide, one of the monosaccharides will form a reducing end, and the other monosaccharide will form a non-reducing end. For convenience, the carbons of the monosaccharide forming the reducing terminus will be denoted as located at positions 1, 2, 3, 4, 5 and 6, while the corresponding carbons of the monosaccharide forming the non-reducing terminus will be denoted as being located at positions 1', 2', 3', 4', 5' and 6', following conventional carbohydrate numbering nomenclature. In the DSLP, the carbon at the 1 position of the non-reducing terminus is linked, through either an ether (—O—) or amino (—NH—) group, to the carbon at the 6' position of the reducing terminus. The phosphate group will be linked to the disaccharide, preferably through the 4' carbon of the non-reducing terminus. Each of the lipid groups will be joined, through either amide (—NH—C(O)—) or ester (—O—C(O)—) linkages to the disaccharide, where the carbonyl group joins to the lipid group. The disaccharide has 7 positions that may be linked to an amide or ester group, namely, positions 2', 3', and 6' of the non-reducing terminus, and positions 1, 2, 3 and 4 of the reducing terminus.

For example, the lipid group has at least three carbons, or at least six carbons, preferably at least 8 carbons, and more preferably at least 10 carbons, where in each case the lipid group has no more than 24 carbons, no more than 22 carbons, or no more than 20 carbons. In one embodiment, the lipid groups taken together provide 60-100 carbons, preferably 70 to 90 carbons. A lipid group may consist solely of carbon and hydrogen atoms, i.e., it may be a hydrocarbyl lipid group, or it may contain one hydroxyl group, i.e., it may be a hydroxyl-substituted lipid group, or it may contain an ester group which is, in turn, joined to a hydrocarbyl lipid or a hydroxyl-substituted lipid group through the carbonyl (—C(O)—) of the ester group, i.e., a ester substituted lipid. A hydrocarbyl lipid group may be saturated or unsaturated, where an unsaturated hydrocarbyl lipid group will have one double bond between adjacent carbon atoms.

The DSLP comprises 3, or 4, or 5, or 6 or 7 lipid groups. In one aspect, the DSLP comprises 3 to 7 lipid groups, while in another aspect the DSLP comprises 4-6 lipids. In one aspect, the lipid group is independently selected from hydrocarbyl lipid, hydroxyl-substituted lipid, and ester substituted lipid. In one aspect, the 1, 4' and 6' positions are substituted with hydroxyl. In one aspect, the monosaccharide units are each glucosamine. The DSLP may be in the free acid form, or in the salt form, e.g., an ammonium salt.

In certain embodiments, the lipid on the DSLP is described by the following: the 3' position is substituted with —O—(CO)—CH2-CH(Ra)(—O—C(O)—Rb); the 2' position is substituted with —NH—(CO)—CH2-CH(Ra)(—O—C(O)—Rb); the 3 position is substituted with —O—(CO)—CH2-CH(OH)(Ra); the 2 position is substituted with —NH—(CO)—CH$_2$—CH(OH)(Ra); where each of Ra and Rb is selected from decyl, undecyl, dodecyl, tridecyl, tetradecyl, wherein each of these terms refer to saturated hydrocarbyl groups. In one embodiment, Ra is undecyl and Rb is tridecyl, where this compound is described in, for example, U.S. Patent Application Publication 2008/0131466 as "GLA." The compound wherein Ra is undecyl and Rb is tridecyl may be used in a stereochemically defined form, as available from, for example, Avanti Polar Lipid as PHAD™ adjuvant.

In one aspect, the DSLP is a mixture of naturally-derived compounds known as 3D-MPL. 3D-MPL adjuvant is produced commercially in a pharmaceutical grade form by GlaxoSmithKline Company as their MPL™ adjuvant. 3D-MPL has been extensively described in the scientific and patent literature, see, e.g., Vaccine Design: the subunit and adjuvant approach, Powell M. F. and Newman, M. J. eds., Chapter 21 Monophosphoryl Lipid A as an adjuvant: past experiences and new directions by Ulrich, J. T. and Myers, K. R., Plenum Press, New York (1995) and U.S. Pat. No. 4,912,094.

In another aspect, the DSLP compound may be described as comprising (i) a diglucosamine backbone having a reducing terminus glucosamine linked to a non-reducing terminus glucosamine through an ether linkage between hexosamine position 1 of the non-reducing terminus glucosamine and hexosamine position 6 of the reducing terminus glucosamine; (ii) an O-phosphoryl group attached to hexosamine position 4 of the non-reducing terminus glucosamine; and (iii) up to six fatty acyl chains; wherein one of the fatty acyl chains is attached to 3-hydroxy of the reducing terminus glucosamine through an ester linkage, wherein one of the fatty acyl chains is attached to a 2-amino of the non-reducing terminus glucosamine through an amide linkage and comprises a tetradecanoyl chain linked to an alkanoyl chain of greater than 12 carbon atoms through an ester linkage, and wherein one of the fatty acyl chains is attached to 3-hydroxy of the non-reducing terminus glucosamine through an ester linkage and comprises a tetradecanoyl chain linked to an alkanoyl chain of greater than 12 carbon atoms through an ester linkage. See, e.g., U.S. Patent Application Publication No. 2008/0131466.

In another aspect, the GLA compound may be a synthetic disaccharide having six lipid groups as described in U.S. patent application publication 2010/0310602.

In another aspect, a DSLP is described by chemical formula (II):

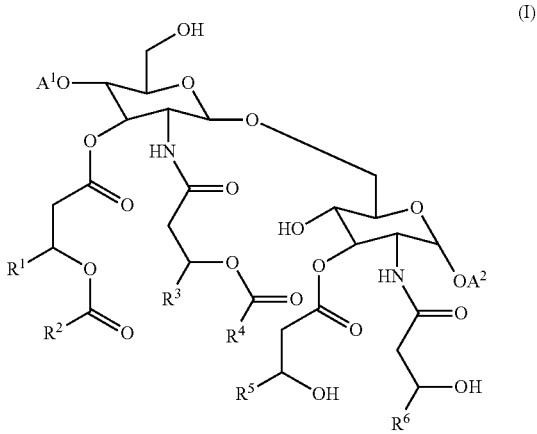

wherein the moieties A1 and A2 are independently selected from the group of hydrogen, phosphate, and phosphate salts. Sodium and potassium are exemplary counterions for the phosphate salts. The moieties R1, R2, R3, R4, R5, and R6 are independently selected from the group of hydrocarbyl having 3 to 23 carbons, represented by C3-C23. For added clarity it will be explained that when a moiety is "independently selected from" a specified group having multiple members, it should be understood that the member chosen for the first moiety does not in any way impact or limit the choice of the member selected for the second moiety. The carbon atoms to which R1, R3, R5 and R6 are joined are asymmetric, and thus may exist in either the R or S stereochemistry. In one embodiment all of those carbon atoms are in the R stereochemistry, while in another embodiment all of those carbon atoms are in the S stereochemistry.

As used herein, "alkyl" means a straight chain or branched, noncyclic or cyclic, unsaturated or saturated aliphatic hydrocarbon containing from 1 to 20 carbon atoms, and in certain preferred embodiments containing from 11 to 20 carbon atoms. Representative saturated straight chain alkyls include methyl, ethyl, n-propyl, n-butyl, n-pentyl, n-hexyl, and the like, including undecyl, dodecyl, tridecyl, tetradecyl, pentadecyl, hexadecyl, heptadecyl, octadecyl, etc.; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like. Cyclic alkyls are also referred to herein as "homocycles" or "homocyclic rings." Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like. For example, "C18-13 alkyl" and "C6-11 alkyl" mean an alkyl as defined above, containing from 8-13 or 6-11 carbon atoms, respectively.

As used herein, "acid functional group" means a functional group capable of donating a proton in aqueous media (i.e. a Brønsted-Lowry acid). After donating a proton, the acid functional group becomes a negatively charged species (i.e. the conjugate base of the acid functional group). Examples of acid functional groups include, but are not limited to: —OP(=O)(OH)$_2$ (phosphate), —OS(=O)(OH)$_2$ (sulfate), —OS(OH)$_2$ (sulfite), —OC(OH)$_2$ (carboxylate), —OC(=O)CH(NH$_2$)CH$_2$C(=O)OH (aspartate), —OC(=O)CH$_2$CH$_2$C(=O)OH (succinate), and —OC(=O)CH$_2$OP(=O)(OH)$_2$ (carboxymethylphosphate).

As used herein, "hydrocarbyl" refers to a chemical moiety formed entirely from hydrogen and carbon, where the arrangement of the carbon atoms may be straight chain or branched, noncyclic or cyclic, and the bonding between adjacent carbon atoms maybe entirely single bonds, that is, to provide a saturated hydrocarbyl, or there may be double or triple bonds present between any two adjacent carbon atoms, i.e., to provide an unsaturated hydrocarbyl, and the number of carbon atoms in the hydrocarbyl group is between 3 and 24 carbon atoms. The hydrocarbyl may be an alkyl, where representative straight chain alkyls include methyl, ethyl, n-propyl, n-butyl, n-pentyl, n-hexyl, and the like, including undecyl, dodecyl, tridecyl, tetradecyl, pentadecyl, hexadecyl, heptadecyl, octadecyl, etc.; while branched alkyls include isopropyl, sec-butyl, isobutyl, tert-butyl, isopentyl, and the like. Representative saturated cyclic hydrocarbyls include cyclopropyl, cyclobutyl, cyclopentyl, cyclohexyl, and the like; while unsaturated cyclic hydrocarbyls include cyclopentenyl and cyclohexenyl, and the like. Unsaturated hydrocarbyls contain at least one double or triple bond between adjacent carbon atoms (referred to as an "alkenyl" or "alkynyl," respectively, if the hydrocarbyl is non-cyclic, and cycloalkeny and cycloalkynyl, respectively, if the hydrocarbyl is at least partially cyclic). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

The compound of formula (II) may be obtained by synthetic methods known in the art, for example, the synthetic methodology disclosed in PCT International Publication No. WO 2009/035528, which is incorporated herein by reference, as well as the publications identified in WO 2009/035528, each of which publications is also incorporated herein by reference. Certain of these compounds may also be obtained commercially.

The DSLP compound may be obtained by synthetic methods known in the art, for example, the synthetic methodology disclosed in PCT International Publication No. WO 2009/035528, which is incorporated herein by reference, as well as the publications identified in WO 2009/035528, where each of those publications is also incorporated herein by reference. A chemically synthesized DSLP compound, e.g., the compound of formula (II), can be prepared in substantially homogeneous form, which refers to a preparation that is at least 80%, at least 85%, at least 90%, at least 95% or at least 96%, 97%, 98% or 99% pure with respect to the DSLP molecules present, e.g., the compounds of formula (II). Determination of the degree of purity of a given preparation can be readily made by those familiar with the appropriate analytical chemistry methodologies, such as by gas chromatography, liquid chromatography, mass spectroscopy and/or nuclear magnetic resonance analysis. DSLP compounds obtained from natural sources are typically not easily made in a chemically pure form, and thus synthetically prepared compounds are preferred for use in the compositions and methods for treating cancer described herein. As discussed previously, certain of the DSLP compounds may be obtained commercially. One such DSLP compound is Product No. 699800 as identified in the catalog of Avanti Polar Lipids, Alabaster Ala., see E1 in combination with E10, below.

In various embodiments, the compound has the chemical structure of formula (II) but the moieties A1, A2, R1, R2, R3, R4, R5, and R6 are selected from subsets of the options previously provided for these moieties, wherein these subsets are identified below by E1, E2, etc.

E1: A1 is phosphate or phosphate salt and A2 is hydrogen.

E2: R1, R3, R5 and R6 are C3-C21 alkyl; and R2 and R4 are C5-C23 hydrocarbyl.

E3: R1, R3, R5 and R6 are C5-C17 alkyl; and R2 and R4 are C7-C19 hydrocarbyl.

E4: R1, R3, R5 and R6 are C7-C15 alkyl; and R2 and R4 are C9-C17 hydrocarbyl.

E5: R1, R3, R5 and R6 are C9-C13 alkyl; and R2 and R4 are C11-C15 hydrocarbyl.

E6: R1, R3, R5 and R6 are C9-C15 alkyl; and R2 and R4 are C11-C17 hydrocarbyl.

E7: R1, R3, R5 and R6 are C7-C13 alkyl; and R2 and R4 are C9-C15 hydrocarbyl.

E8: R1, R3, R5 and R6 are C11-C20 alkyl; and R2 and R4 are C12-C$_{20}$ hydrocarbyl.

E9: R1, R3, R5 and R6 are C11 alkyl; and R2 and R4 are C13 hydrocarbyl.

E10: R1, R3, R5 and R6 are undecyl and R2 and R4 are tridecyl.

In certain embodiments, each of E2 through E10 is combined with embodiment E1, and/or the hydrocarbyl groups of E2 through E9 are alkyl groups, preferably straight chain alkyl groups.

U.S. Patent Publication No. 2008/0131466 that provides formulations, such as aqueous formulation (AF) and stable emulsion formulations (SE) for GLA compounds, wherein these formulations may be used for any of the compounds of formula (I).

The invention provides compositions for stimulating an immune response in a cancer patient. Typically, immune responses may be detected by any of a variety of well-known parameters, including but not limited to in vivo or in vitro determination of: soluble immunoglobulins or antibodies; soluble mediators such as cytokines, lymphokines, chemokines, hormones, growth factors and the like as well as other soluble small peptide, carbohydrate, nucleotide and/or lipid mediators; cellular activation state changes as determined by altered functional or structural properties of cells of the immune system, for example cell proliferation, altered motility, induction of specialized activities such as specific gene expression or cytolytic behavior; cellular differentiation by cells of the immune system, including altered surface antigen expression profiles or the onset of apoptosis (programmed cell death); an increase in cytotoxic T-cells, activated macrophages or natural killer cells; or any other criterion by which the presence of an immune response may be detected.

Procedures for performing these and similar assays are widely known and may be found, for example in Lefkovits (*Immunology Methods Manual: The Comprehensive Sourcebook of Techniques*, 1998; see also *Current Protocols in Immunology*; see also, e.g., Weir, *Handbook of Experimental Immunology*, 1986 Blackwell Scientific, Boston, Mass.; Mishell and Shigii (eds.) *Selected Methods in Cellular Immunology*, 1979 Freeman Publishing, San Francisco, Calif.; Green and Reed, 1998 *Science* 281:1309 and references cited therein.).

Detection of the proliferation of tumor-reactive T cells may be accomplished by a variety of known techniques. For example, T cell proliferation can be detected by measuring the rate of DNA synthesis, and tumor specificity can be determined by controlling the stimuli (such as, for example, a specific desired tumor- or a control antigen-pulsed antigen presenting cells) to which candidate tumor-reactive T cells are exposed. T cells which have been stimulated to proliferate exhibit an increased rate of DNA synthesis. A typical way to measure the rate of DNA synthesis is, for example, by pulse-labeling cultures of T cells with tritiated thymidine, a nucleoside precursor which is incorporated into newly synthesized DNA. The amount of tritiated thymidine incorporated can be determined using a liquid scintillation spectrophotometer. Other ways to detect T cell proliferation include measuring increases in interleukin-2 (IL-2) production, Ca$^{2+}$ flux, or dye uptake, such as 3-(4,5-dimethylthiazol-2-yl)-2,5-diphenyl-tetrazolium. Alternatively, synthesis of lymphokines (such as interferon-gamma) can be measured or the relative number of T cells that can respond to a particular antigen may be quantified.

Detection of antibody production (e.g., tumor specific antibody production) may be achieved, for example, by assaying a sample (e.g., an immunoglobulin containing sample such as serum, plasma or blood) from a host treated with a GLA composition according to the present invention using in vitro methodologies such as radioimmunoassay (RIA), enzyme linked immunosorbent assays (ELISA), equilibrium dialysis or solid phase immunoblotting including Western blotting. In preferred embodiments ELISA assays may further include tumor antigen-capture immobilization of a target tumor antigen with a solid phase monoclonal antibody specific for the antigen, for example, to enhance the sensitivity of the assay. Elaboration of soluble mediators (e.g., cytokines, chemokines, lymphokines, prostaglandins, etc.) may also be readily determined by enzyme-linked immunosorbent assay (ELISA), for example, using methods, apparatus and reagents that are readily available from commercial sources (e.g., Sigma, St. Louis, Mo.; see also R & D Systems 2006 Catalog, R & D Systems, Minneapolis, Minn.).

Any number of other immunological parameters may be monitored using routine assays that are well known in the art. These may include, for example, antibody dependent cell-mediated cytotoxicity (ADCC) assays, secondary in vitro antibody responses, flow immunocytofluorimetric analysis of various peripheral blood or lymphoid mononuclear cell subpopulations using well established marker antigen systems, immunohistochemistry or other relevant assays. These and other assays may be found, for example, in Rose et al. (Eds.), *Manual of Clinical Laboratory Immunology*, 5$^{th}$ Ed., 1997 American Society of Microbiology, Washington, D.C.

Accordingly it is contemplated that the GLA compositions provided herein will be capable of eliciting or enhancing in a cancer patient at least one immune response that is selected from a T$_H$1-type T lymphocyte response, a T$_H$2-type T lymphocyte response, a cytotoxic T lymphocyte (CTL) response, an antibody response, a cytokine response, a lymphokine response, a chemokine response, and an inflammatory response. In certain embodiments, the immune response may include suppression of regulatory T cells, such as a decrease in the number of CD4+FoxP3+ T regulatory cells. In another embodiment, the immune response comprises an increase in the number of intratumoral CD8+ T effector cells. In certain embodiments the immune response may comprise at least one of production of one or a plurality of cytokines wherein the cytokine is selected from interferon-gamma (IFN-γ), tumor necrosis factor-alpha (TNF-α), production of one or a plurality of interleukins wherein the interleukin is selected from IL-1, IL-2, IL-3, IL-4, IL-6, IL-8, IL-10, IL-12, IL-13, IL-16, IL-18 and IL-23, production of one or a plurality of chemokines wherein the chemokine is selected from MIP-1α, MIP-1β, RANTES, CCL4 and CCL5, and a lymphocyte response that is selected from a memory T cell response, a memory B cell response, an effector T cell response, a cytotoxic T cell response and an effector B cell response. See, e.g., WO 94/00153; WO 95/17209; WO 96/02555; U.S. Pat. Nos. 6,692,752; 7,084,256; 6,977,073; 6,749,856; 6,733,763; 6,797,276; 6,752,995; 6,057,427; 6,472,515; 6,309,847; 6,969,704; 6,120,769; 5,993,800; 5,595,888; Smith et al., 1987 J Biol. Chem. 262:6951; Kriegler et al., 1988 Cell 53:45 53; Beutler et al., 1986 Nature 320:584; U.S. Pat. Nos. 6,991, 791; 6,654,462; 6,375,944.

Pharmaceutical Compositions, Delivery and Methods of Use

In examples of embodiments, the GLA compounds described herein are present in a composition in an amount of 0.1-10 µg/dose, or 0.1-20 µg/dose, 0.1-30 µg/dose, 0.1-40 µg/dose, or 0.1-50 µg/dose, or 1-20 µg/dose, or 1-30 µg/dose, or 1-40 µg/dose, or 1-50 µg/dose, or 0.2-5 µg/dose, or in an amount of 0.5-2.5 µg/dose, or in an amount of 0.5-8 µg/dose or 0.5-15 µg/dose. Doses may be, for example, 0.5 µg/dose, 0.6 µg/dose, 0.7 µg/dose, 0.8 µg/dose, 0.9 µg/dose, 1.0

μg/dose, 2.0 μg/dose, 3.0 μg/dose, 3.5 μg/dose, 4.0 μg/dose, 4.5 μg/dose, 5.0 μg/dose, 5.5 μg/dose, 6.0 μg/dose, 6.5 μg/dose, 7.0 μg/dose, 7.5 μg/dose, 8.0 μg/dose, 9.0 μg/dose, 10.0 μg/dose, 11.0 μg/dose, 12.0 μg/dose, 13.0 μg/dose, 14.0 μg/dose, or 15.0 μg/dose. Doses may be adjusted depending upon the body mass, body area, weight, blood volume of the subject, or route of delivery. In one embodiment, 2 μg, 3 μg, 4 μg, 5 μg, 6 μg, 7 μg, 8 μg, 9 μg, 10 μg, 11 μg, or 12 μg of GLA in 1 ml is administered intratumorally. In this regard, the 1 mL dose of GLA may be injected in equal amounts in multiple zones of the tumor. In certain embodiments, about 0.01 μg/kg to about 100 mg/kg body weight of GLA will be administered, typically by the intradermal, intratumoral, subcutaneous, intramuscular or intravenous route, or by other routes. In certain embodiments, the dosage of GLA is about 0.1 μg/kg to about 1 mg/kg, and in certain embodiments, ranges from about 0.1 μg/kg, 0.2 μg/kg, 0.3 μg/kg, 0.4 μg/kg, 0.5 μg/kg, 0.6 μg/kg, 0.7 μg/kg, 0.8 μg/kg, 0.9 μg/kg, 1 μg/kg, 2 μg/kg, 3 μg/kg, 4 μg/kg, 5 μg/kg, 6 μg/kg, 7 μg/kg, 8 μg/kg, 9 μg/kg, 10 μg/kg to about 200 μg/kg. It will be evident to those skilled in the art that the number and frequency of administration will be dependent upon the response of the host. As described herein, the appropriate dose may also depend upon the patient's (e.g., human) condition, that is, stage of the disease, general health status, as well as age, gender, and weight, and other factors familiar to a person skilled in the medical art. As noted elsewhere herein, the GLA compositions described herein do not include antigen.

Pharmaceutical compositions may be formulated for any appropriate manner of administration, including, for example, topical, oral, enteral, nasal (i.e., intranasal), inhalation, intrathecal, rectal, vaginal, intraocular, subconjunctival, buccal, sublingual, intrapulmonary, intradermal, intranodal, intratumoral, transdermal, or parenteral administration, including subcutaneous, percutaneous, intravenous, intramuscular, intrasternal, intracavernous, intrameatal, intratumoral, intracranial, intraspinal or intraurethral injection or infusion. Methods of administration are described in greater detail herein.

Compositions comprising a GLA as described herein and optionally further comprising one or more additional therapeutic agents, may be formulated for delivery by any route that provides an effective dose of the GLA or the one or more additional therapeutic agents. Such administrations methods include oral administration or delivery by injection and may be in the form of a liquid. A liquid pharmaceutical composition may include, for example, one or more of the following: a sterile diluent such as water for injection, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral preparation can be enclosed in ampoules, disposable syringes or multiple dose vials made of glass or plastic. The use of physiological saline is preferred, and an injectable pharmaceutical composition is preferably sterile.

The GLA composition may further comprise at least one physiologically (or pharmaceutically) acceptable or suitable excipient. Any physiologically or pharmaceutically suitable excipient or carrier (i.e., a non-toxic material that does not interfere with the activity of the active ingredient) known to those of ordinary skill in the art for use in pharmaceutical compositions may be employed in the compositions described herein. Exemplary excipients include diluents and carriers that maintain stability and integrity of proteins. Excipients for therapeutic use are well known, and are described, for example, in Remington: The Science and Practice of Pharmacy (Gennaro, 21st Ed. Mack Pub. Co., Easton, Pa. (2005)), and are described in greater detail herein.

"Pharmaceutically acceptable carriers" for therapeutic use are well known in the pharmaceutical art, and are described, for example, in Remingtons Pharmaceutical Sciences, Mack Publishing Co. (A. R. Gennaro edit. 1985). For example, sterile saline and phosphate buffered saline at physiological pH may be used. Preservatives, stabilizers, dyes and even flavoring agents may be provided in the pharmaceutical composition. For example, sodium benzoate, sorbic acid and esters of p hydroxybenzoic acid may be added as preservatives. Id. at 1449. In addition, antioxidants and suspending agents may be used. Id.

"Pharmaceutically acceptable salt" refers to salts of the compounds of the present invention derived from the combination of such compounds and an organic or inorganic acid (acid addition salts) or an organic or inorganic base (base addition salts). The compositions of the present invention may be used in either the free base or salt forms, with both forms being considered as being within the scope of the present invention.

The pharmaceutical compositions may be in any form which allows for the composition to be administered to a patient. For example, the composition may be in the form of a solid, liquid or gas (aerosol). The pharmaceutical compositions may be administered by any route. Typical routes of administration include, without limitation, oral, sublingual, buccal, topical, parenteral, rectal, vaginal, intranasal (e.g., as a spray) and intrapulmonary administration. The term parenteral as used herein includes iontophoretic (e.g., U.S. Pat. Nos. 7,033,598; 7,018,345; 6,970,739), sonophoretic (e.g., U.S. Pat. Nos. 4,780,212; 4,767,402; 4,948,587; 5,618,275; 5,656,016; 5,722,397; 6,322,532; 6,018,678), thermal (e.g., U.S. Pat. Nos. 5,885,211; 6,685,699), passive transdermal (e.g., U.S. Pat. Nos. 3,598,122; 3,598,123; 4,286,592; 4,314,557; 4,379,454; 4,568,343; 5,464,387; UK Pat. Spec. No. 2232892; U.S. Pat. Nos. 6,871,477; 6,974,588; 6,676,961), microneedle (e.g., U.S. Pat. Nos. 6,908,453; 5,457,041; 5,591,139; 6,033,928) administration and also subcutaneous injections, intravenous, intramuscular, intrasternal, intracavernous, intrathecal, intranodal, intrameatal, intraurethral, intratumoral injection or infusion techniques. In a particular embodiment, a composition as described herein is administered intradermally by a technique selected from iontophoresis, microcavitation, sonophoresis or microneedles.

The pharmaceutical composition is formulated so as to allow the active ingredients contained therein to be bioavailable upon administration of the composition to a patient. Compositions that will be administered to a patient take the form of one or more dosage units, where for example, a tablet may be a single dosage unit, and a container of one or more compounds of the invention in aerosol form may hold a plurality of dosage units.

For oral administration, an excipient and/or binder may be present. Examples are sucrose, kaolin, glycerin, starch dextrins, sodium alginate, carboxymethylcellulose and ethyl cellulose. Coloring and/or flavoring agents may be present. A coating shell may be employed.

The composition may be in the form of a liquid, e.g., an elixir, syrup, solution, emulsion or suspension. The liquid may be for oral administration or for delivery by injection, as two examples. When intended for oral administration, preferred compositions contain one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

A liquid pharmaceutical composition as used herein, whether in the form of a solution, suspension or other like form, may include one or more of the following carriers or excipients: sterile diluents such as water for injection, saline solution, preferably physiological saline, Ringer's solution, isotonic sodium chloride, fixed oils such as squalene, squalane, mineral oil, a mannide monooleate, cholesterol, and/or synthetic mono or digylcerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. An injectable pharmaceutical composition is preferably sterile.

In a particular embodiment, a composition of the invention comprises a stable aqueous suspension of less than 0.2 um and further comprises at least one component selected from the group consisting of phospholipids, fatty acids, surfactants, detergents, saponins, fluorodated lipids, and the like. Such a stable aqueous formulation may be a micellar formulation.

In another embodiment, a composition of the invention is formulated in a manner which can be aerosolized, either as a powder or liquid formulation.

It may also be desirable to include other components in a pharmaceutical composition, such as including but not limited to water-in-oil emulsions, biodegradable oil vehicles, oil-in-water emulsions, liposomes, micellar components, microparticles, biodegradable microcapsules, and liposomes.

In certain embodiments, the GLA compositions are formulated as described in U.S. Pat. Nos. 8,273,361; 8343,512; or as described in published international applications WO2008/153541; WO2009/143457, with the exception being that in the present invention no antigen is included. Other suitable formulations are described in WO2013/119856, again without including any antigen.

In specific embodiments, compositions comprising GLA as described herein comprise a stable oil-in-water emulsion and a metabolizable oil. In a particular embodiment, a composition of the invention comprises an emulsion of oil in water wherein the GLA is incorporated in the oil phase. In certain embodiments, the oil phase of the emulsion comprises a metabolizable oil. The meaning of the term metabolizable oil is well known in the art. Metabolizable can be defined as "being capable of being transformed by metabolism" (Dorland's illustrated Medical Dictionary, W. B. Saunders Company, 25th edition (1974)). The oil may be any plant oil, vegetable oil, fish oil, animal oil or synthetic oil, which is not toxic to the recipient and is capable of being transformed by metabolism. Nuts (such as peanut oil), seeds, and grains are common sources of vegetable oils. Synthetic oils may also be used.

In certain embodiments, additional immunostimulatory substances may be included in the compositions described herein and may include N-acetylmuramyl-L-alanine-D-isoglutamine (MDP), glucan, IL 12, GM CSF, interferon-γ and IL 12.

While any suitable carrier known to those of ordinary skill in the art may be employed in the pharmaceutical compositions of this invention, the type of carrier will vary depending on the mode of administration and whether a sustained release is desired. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109. In this regard, it is preferable that the microsphere be larger than approximately 25 microns.

Compositions comprising GLA may also contain diluents such as buffers, antioxidants such as ascorbic acid, carbohydrates including glucose, sucrose or dextrins, chelating agents such as EDTA, glutathione and other stabilizers and excipients. Neutral buffered saline or saline mixed with nonspecific serum albumin are exemplary appropriate diluents. Preferably, product may be formulated as a lyophilizate using appropriate excipient solutions (e.g., sucrose) as diluents.

The GLA compositions may be intended for topical administration, in which case the carrier may suitably comprise a solution, emulsion, ointment or gel base. The base, for example, may comprise one or more of the following: petrolatum, lanolin, polyethylene glycols, beeswax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

The compositions provided herein can be in various forms, e.g., in solid, liquid, powder, aqueous, or lyophilized form.

Compositions comprising a GLA as described herein may also be administered simultaneously with, prior to, or after administration of one or more other therapeutic agents. In this regard, the one or more additional therapeutic agents does not include antigen, e.g., a tumor antigen. Thus, the GLA compositions described herein may comprise other therapeutic agents and/or acceptable carriers or excipients but the compositions do not comprise and are not administered in conjunction with antigen. To the extent GLA compositions as described herein are formulated with one or more therapeutic agents, carriers or excipients, such formulated compositions do not comprise an antigen (e.g., an antigen is not added as a component of the formulation).

Such combination therapy may include administration of a single pharmaceutical dosage formulation which contains a GLA and one or more additional active agents, as well as administration of compositions comprising a GLA of the invention and each active agent in its own separate pharmaceutical dosage formulation. For example, a composition comprising a GLA and the other active agent can be administered to the patient together in a single enteral (e.g., oral) dosage composition such as a tablet or capsule, or each agent administered in separate enteral (e.g., oral) dosage formulations. Similarly, compositions comprising a GLA and the other active agent can be administered to the patient together in a single parenteral (e.g., any of the parenteral routes known and described herein, such as, subcutaneous, intradermal, intranodal, intratumoral or intramuscular) dosage composition such as in a saline solution or other physiologically acceptable solution, or each agent administered in separate parenteral dosage formulations. The combination therapies as described herein can be administered by the same route or may be administered using different routes (e.g., intratumoral GLA injection combined with intratumoral injection of one or more other therapeutic agents; or intratumoral GLA injection combined with intramuscular, intravenous, subcutaneous or other route of administration of one or more other therapeutic agents; any combination of administration route is contemplated for use with the combination therapies described herein). Where separate dosage formulations are used, the compositions comprising a GLA and one or more additional active agents can be administered at essentially the same time, i.e., concurrently, or at separately staggered times, i.e., sequentially and in any order; combination therapy is understood to include all these regimens.

Thus, in certain embodiments, also contemplated is the administration of compositions comprising a GLA of this disclosure in combination with one or more other therapeutic agents (e.g. other anti-cancer agents, or other palliative or adjunctive therapy). In certain embodiments, such therapeutic agents may be accepted in the art as a standard treatment for a particular cancer as described herein. Exemplary therapeutic agents contemplated include cytokines, growth factors, steroids, NSAIDs, DMARDs, anti-inflammatories, immune checkpoint inhibitors, chemotherapeutics, radiotherapeutics, or other active and ancillary agents.

In one embodiment, compositions comprising a GLA are administered in combination with one or more cancer therapeutic agents, including one or more chemotherapeutic agents. Examples of cancer therapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimeterxate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®., Rhne-Poulenc Rorer, Antony, France); chlorambucil; gemcitabine; 6-thioguanine; mercaptopurine; methotrexate; platinum analogs such as cisplatin and carboplatin; vinblastine; trastuzumab, docetaxel, platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid derivatives such as Targretin™ (bexarotene), Panretin™ (alitertinoin); ONTAK™ (denileukin diftitox); esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above. Further cancer therapeutic agents include sorafenib and other protein kinase inhibitors such as afatinib, axitinib, bevacizumab, cetuximab, crizotinib, dasatinib, erlotinib, fostamatinib, gefitinib, imatinib, lapatinib, lenvatinib, mubritinib, nilotinib, panitumumab, pazopanib, pegaptanib, ranibizumab, ruxolitinib, trastuzumab, vandetanib, vemurafenib, and sunitinib; sirolimus (rapamycin), everolimus and other mTOR inhibitors.

In another embodiment, the GLA compositions herein are administered in combination with another immunostimulatory agent. Such immunostimulatory agents include, but are not limited to, N-acetylmuramyl-L-alanine-D-isoglutamine (MDP), glucan, IL-12, GM-CSF, interferon-γ and anti-CD40 antibodies or other antibodies that bind to and activate co-stimulatory pathways (e.g., CD28, ICOS, OX40, CD27 and the like).

In one embodiment, the GLA compositions herein are administered in combination with one or more immune checkpoint inhibitors. Immune checkpoints refer to a variety of inhibitory pathways of the immune system that are crucial for maintaining self-tolerance and for modulating the duration and amplitude of an immune responses. Tumors use certain immune-checkpoint pathways as a major mechanism of immune resistance, particularly against T cells that are specific for tumor antigens. (see., e.g., Pardoll, 2012 Nature 12:252; Chen and Mellman 2013 Immunity 39:1). The present disclosure provides immune checkpoint inhibitors that can be administered in combination with the GLA compositions without antigen. Such combination therapies work in concert to enhance an anti-cancer immune response. Certain viruses have also developed mechanisms to co-opt immune checkpoint pathways. Therefore, in certain embodiments, such combination therapy may be used to enhance an anti-viral immune response.

Immune checkpoint inhibitors include any agent that blocks or inhibits in a statistically significant manner, the inhibitory pathways of the immune system. Such inhibitors may include small molecule inhibitors or may include antibodies, or antigen binding fragments thereof, that bind to and block or inhibit immune checkpoint receptors or antibodies that bind to and block or inhibit immune checkpoint receptor ligands. Illustrative immune checkpoint molecules that may be targeted for blocking or inhibition include, but are not limited to, CTLA-4, 4-1BB (CD137), 4-1BBL (CD137L), PDL1, PDL2, PD1, B7-H3, B7-H4, BTLA, HVEM, TIM3, GAL9, LAG3, TIM3, B7H3, B7H4, VISTA, KIR, 2B4 (belongs to the CD2 family of molecules and is expressed on all NK, γδ, and memory $CD8^+$ (αβ) T cells), CD160 (also referred to as BY55) and CGEN-15049 Immune checkpoint inhibitors include antibodies, or antigen binding fragments thereof, or other binding proteins, that bind to and block or inhibit the activity of one or more of CTLA-4, PDL1, PDL2, PD1, B7-H3, B7-H4, BTLA, HVEM, TIM3, GAL9, LAG3, TIM3, B7H3, B7H4, VISTA, KIR, 2B4, CD160 and CGEN-15049. Illustrative immune checkpoint inhibitors include Tremelimumab (CTLA-4 blocking antibody), anti-OX40, PD-L1 monoclonal Antibody (Anti-B7-H1; MEDI4736), MK-3475 (PD-1 blocker), Nivolumab (anti-PD1 antibody), CT-011 (anti-PD1 antibody), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody) and Yervoy/ipilimumab (anti-CTLA-4 checkpoint inhibitor).

In a further embodiment, the GLA compositions herein are administered in combination with other TLR4 agonists, or a TLR8 agonist, or a TLR9 agonist. Such an agonist may be selected from peptidoglycan, polyI:C, CpG, 3M003, flagellin, and *Leishmania* homolog of eukaryotic ribosomal elongation and initiation factor 4a (LeIF).

In an additional embodiment, the GLA compositions herein are administered in combination with a cytokine. By "cytokine" is meant a generic term for proteins released by one cell population that act on another cell as intercellular mediators. Examples of such cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines.

In certain embodiments, the compositions comprising GLA as described herein may be administered in combination with chloroquine, a lysosomotropic agent that prevents endosomal acidification and which inhibits autophagy induced by tumor cells to survive accelerated cell growth and nutrient deprivation. More generally, the compositions comprising GLA as described herein may be administered in combination with therapeutic agents that act as autophagy inhibitors, radio sensitizers or chemo sensitizers, such as chloroquine, misonidazole, metronidazole, and hypoxic cytotoxins, such as tirapazamine. In this regard, such combinations of a GLA with chloroquine or other radio or chemo sensitizer, or autophagy inhibitor, can be used in further combination with other cancer therapeutic agents or with radiation therapy.

In another embodiment, the compositions comprising GLA as described herein may be administered in combination with small molecule drugs which are known to result in killing of tumor cells with concomitant activation of immune responses, termed "immunogenic cell death", such as cyclophosphamide, doxorubicin, oxaliplatin and mitoxantrone. Furthermore, combinations with drugs known to enhance the immunogenicity of tumor cells such as patupilone (epothilone B), epidermal-growth factor receptor (EGFR)-targeting monoclonal antibody 7A7.27, histone deacetylase inhibitors (e.g., vorinostat, romidepsin, panobinostat, belinostat, and entinostat), the n3-polyunsaturated fatty acid docosahexaenoic acid, furthermore proteasome inhibitors (e.g. bortezomib), shikonin (the major constituent of the root of Lithospermum erythrorhizon,) and oncolytic viruses, such as TVec (talimogene laherparepvec). In other embodiments, the compositions comprising GLA as described herein may be administered in combination with epigenetic therapies, such as DNA methyltransferase inhibitors (e.g. Decitabine, 5-aza-2'-deoxycytidine) which may be administered locally or systemically.

In another embodiment, the compositions comprising a GLA as described herein may be administered in combination with one or more antibodies that increase ADCC uptake of tumor by DCs. Thus, the present invention contemplates combining compositions comprising a GLA with any molecule that induces or enhances the ingestion of a tumor cell or its fragments by an antigen presenting cell and subsequent presentation of tumor antigens to the immune system. These molecules include agents that induce receptor binding (such as Fc or mannose receptors) and transport into the antigen presenting cell such as antibodies, antibody-like molecules, multi-specific multivalent molecules and polymers. Such molecules may either be administered intratumorally with the composition comprising GLA, or administered by a different route. For example, a composition comprising GLA as described herein may be administered intratumorally in conjunction with intratumoral injection of rituximab, cetuximab, trastuzumab, Campath, panitumumab, ofatumumab, brentuximab, pertuzumab, Ado-trastuzumab emtansine, Obinutuzumab, anti-HER1, -HER2, or -HER3 antibodies (e.g., MEHD7945A; MM-111; MM-151; MM-121; AMG888), anti-EGFR antibodies (e.g. Nimotuzumab, ABT-806), or other like antibodies. Any multivalent scaffold that is capable of engaging Fc receptors and other receptors that can induce internalization may be used in the combination therapies described herein—e.g. peptides and/or proteins capable of binding targets that are linked to Fc fragments or polymers capable of engaging receptors.

In certain embodiments, the combination of GLA with such antibodies may be further combined with an antibody that promotes a co-stimulatory signal (e.g., by blocking inhibitory pathways), such as anti-CTLA-4, or that activates co-stimulatory pathways such as an anti-CD 40, anti-CD28, anti-ICOS, anti-OX40, anti-CD27 antibodies and the like.

The compositions comprising GLA may be administered alone or in combination with other known cancer treatments, such as radiation therapy, immune checkpoint inhibitors, chemotherapy or other cancer therapeutic agents, transplantation, immunotherapy, hormone therapy, photodynamic therapy, etc. The compositions may also be administered in combination with antibiotics.

The present disclosure relates to the discovery that GLA can be used as a monotherapy (e.g., not as a vaccine adjuvant) for the treatment of cancer. Thus, the present disclosure provides a method of treating a mammal who suffers from cancer comprising administering an effective amount of a composition comprising GLA, wherein the composition does not comprise an antigen (e.g., does not comprise a tumor antigen). According to the present disclosure, the phrase "does not comprise an antigen" or "does not comprise antigen" refers to a composition that does not include an antigen for the purpose of eliciting an antigen-specific immune response. To that end, a composition that is substantially devoid of antigen or a composition that includes a trace amount of antigen is contemplated according to the present disclosure, so long as the amount of antigen present is insufficient to elicit a specific immune response to that antigen.

The GLA compositions described herein may be useful for the treatment of a variety of cancers. In one embodiment, the compositions comprising a GLA as described herein, wherein the composition does not comprise an antigen, may be useful for the treatment of a variety of solid tumors, i.e., carcinomas, sarcomas, and lymphomas. In certain embodiments, the cancer is a primary solid tumor, and in certain other embodiments a cancer is a metastatic or secondary solid tumor. In certain related embodiments, the cancer is selected from melanoma, lung cancer, cervical cancer, ovarian cancer, uterine cancer, breast cancer, liver cancer, gastric cancer, colon cancer, prostate cancer, pancreatic cancer, kidney cancer, bladder cancer, brain cancer, fibrosarcoma, myxosarcoma, liposarcoma, chondrosarcoma, osteogenic sarcoma, chordoma, angiosarcoma, endothelio sarcoma, lymphangiosarcoma, pseudomyxoma petitonei, lymphangioendotheliosarcoma, synovioma, mesothelioma, Ewing's tumor, leiomyosarcoma, rhabdomyosarcoma, colon carcinoma, pancreatic cancer, squamous cell carcinoma, basal cell carcinoma, adenocarcinoma, Merkel cell carcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma and Wilms' tumor. In certain other related embodiments the cancer cell originates in a cancer that is selected from testicular tumor, lung carcinoma, small cell lung carcinoma, bladder carcinoma, epithelial carcinoma, glioma, glioblastoma multiforme, astrocytoma, plasmocytoma, medulloblastoma, craniopharyngioma, ependymoma, pinealoma, hemangioblastoma, acoustic neuroma, oliodendroglioma, meningioma, melanoma, neuroblastoma, retinoblastoma, leukemia, lymphoma, non-Hodgkin's lymphoma, multiple myeloma, Waldenstrom's macroglobulinemia or other cancers. Thus, the methods described herein include methods for the treatment of, ameliorating the symptoms of, and inhibiting metastasis of cancer comprising administering an effective amount of a composition comprising a GLA as described herein, wherein the composition does not comprise an antigen. As described herein, the methods described herein include methods for the treatment of, ameliorating the symptoms of, and inhibiting metastasis of cancer comprising administering an effective amount of a composition comprising a GLA as described herein, wherein the composition does not comprise an antigen, in combination with a therapeutically effective amount of one or more other therapeutic agents. In one embodiment, the methods herein comprise a method of treating a cancer comprising administering a composition comprising a GLA wherein the composition does not comprise an antigen, and a composition comprising a checkpoint inhibitor or an antibody that stimulates a co-stimulatory pathway. In one embodiment, the method involves intratumoral injection of the composition comprising GLA, wherein the composition does not comprise an antigen, and co-administering intratumorally, one or more other therapeutic agents, such as a checkpoint inhibitor or an antibody that stimulates a co-stimulatory pathway (e.g., anti-CD40 antibodies). In one embodiment of the method, the GLA composition and the therapeutic agent, e.g., a checkpoint inhibitor, are administered at the same time. In another embodiment of the method, the GLA composition and the therapeutic agent, e.g., a checkpoint inhibitor, antibody that stimulates a co-stimulatory pathway, cytokine or other therapeutic agent, are administered intratumorally at a separate time, where e.g., the checkpoint inhibitor is administered either before or after injection of the GLA composition. In a further embodiment, the method involves intratumoral injection of the composition comprising GLA, without antigen, and administering the therapeutic agent such as, but not limited to, a checkpoint inhibitor or anti-CD40 antibody, at about the same time but by a different route (e.g., intraperitoneally, i.v., i.m.). Thus, in certain embodiments of the present invention, the GLA compositions and other therapeutic agent, such as but not limited to, checkpoint inhibitor or anti-CD40 antibody compositions, may be administered concurrently or sequentially in any order and may be administered at the same site by the same route or may be administered at different sites by different routes.

Kits may contain one or more doses of GLA compositions, optionally in a container such as a vial or blister or capsule or pre-filled syringe, and optionally one or more other therapeutic agents. A kit may also contain instructions. Instructions typically describe methods for administration, including methods for determining the proper state of the subject, the proper dosage amount, and the proper administration method, for administering the composition. Instructions can also include guidance for monitoring the subject over the duration of the treatment time.

Kits provided herein also can include devices for administration of each of the compositions described herein to a subject. Any of a variety of devices known in the art for administering medications can be included in the kits provided herein. Exemplary devices include, but are not limited to, a hypodermic needle, an intravenous needle, microneedle, a catheter, a needle-less injection device, an aerosolizer, inhaler or nebulizer or atomizer or microspray device, and a liquid dispenser, such as an eyedropper. Typically, the device for administering a composition is compatible with the active components of the kit.

Embodiments of the invention include, but are not limited to, the following.

1. A method of treating a mammal who suffers from cancer, comprising administering an effective amount of a composition comprising GLA, said composition comprising:

(a) GLA of the formula:

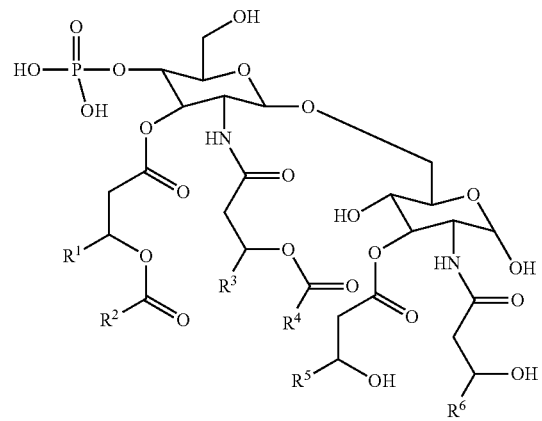

wherein:

R$^1$, R$^3$, R$^5$ and R$^6$ are C$_{11}$-C$_{20}$ alkyl; and

R$^2$ and R$^4$ are C$_{12}$-C$_{20}$ alkyl; and (b) a pharmaceutically acceptable carrier or excipient;

wherein the composition does not comprise antigen.

2. An effective amount of a composition comprising GLA, said composition comprising:

(a) GLA of the formula:

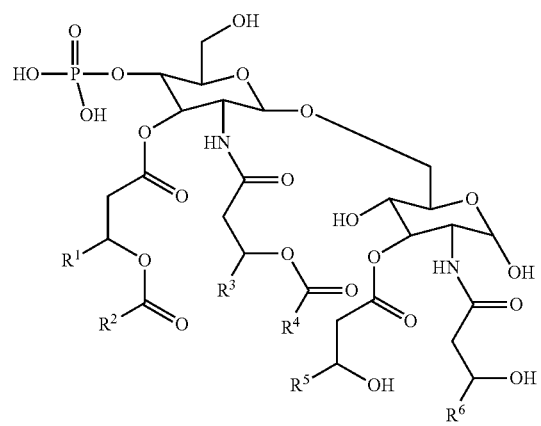

wherein:

R$^1$, R$^3$, R$^5$ and R$^6$ are C$_{11}$-C$_{20}$ alkyl; and

R$^2$ and R$^4$ are C$_{12}$-C$_{20}$ alkyl; and (b) a pharmaceutically acceptable carrier or excipient;

wherein the composition does not comprise antigen; for use in the treatment of a cancer in a mammal.

3. The use of an effective amount of a composition comprising GLA, said composition comprising:

(a) GLA of the formula:

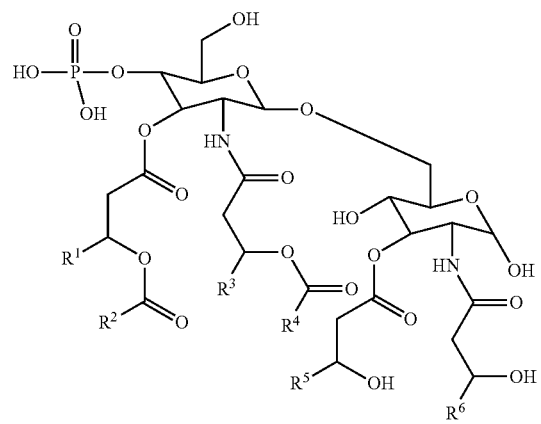

wherein:

R$^1$, R$^3$, R$^5$ and R$^6$ are C$_{11}$-C$_{20}$ alkyl; and

R$^2$ and R$^4$ are C$_{12}$-C$_{20}$ alkyl; and (b) a pharmaceutically acceptable carrier or excipient;

wherein the composition does not comprise antigen; for the manufacture of a medicament for the treatment of a cancer in a mammal.

4. Any of the preceding embodiments, wherein R$^1$, R$^3$, R$^5$ and R$^6$ are undecyl and R$^2$ and R$^4$ are tridecyl.

5. Any of the preceding embodiments, wherein the mammal is human.

6. Any of the preceding embodiments, wherein the composition is an aqueous formulation.

7. Any of the preceding embodiments, wherein the composition is in the form of an oil-in-water emulsion, a water-in-oil emulsion, liposome, micellar formulation, or a microparticle.

8. Any of the preceding embodiments, wherein the cancer comprises a solid tumor. In any of the embodiments described herein, the solid tumor is a carcinoma, a sarcoma or a lymphoma. In any of the embodiments described herein, the solid tumor is a primary or a secondary solid tumor.

9. Any of the preceding embodiments, wherein the cancer is selected from the group consisting of, melanoma, Merkel cell carcinoma, lung cancer, cervical cancer, ovarian cancer, uterine cancer, breast cancer, liver cancer, gastric cancer, prostate cancer, colon cancer, kidney cancer, bladder cancer, brain cancer, and pancreatic cancer.

10. Any of the preceding embodiments, wherein the composition is administered by subcutaneous, intradermal, intramuscular, intratumoral, or intravenous injection.

11. Any of the preceding embodiments, wherein the composition is administered intranasally or intrapulmonary.

12. Any of the preceding embodiments, wherein the composition is administered in conjunction with one or more additional therapeutic agents or treatments.

13. Embodiment 12, wherein the therapeutic agents is an immune checkpoint inhibitor.

14. Embodiment 12 or 13, wherein the therapeutic agent is an antibody that activates a co-stimulatory pathway. An exemplary such antibody is an anti-CD40 antibody.

15. Embodiment 12 or 13, wherein the therapeutic agent is a cancer therapeutic agent such as a chemotherapeutic agent.

16. Embodiment 15 wherein the cancer therapeutic agent is selected from the group consisting of taxotere, carboplatin, trastuzumab, epirubicin, cyclophosphamide, cisplatin, docetaxel, doxorubicin, etoposide, 5-FU, gemcitabine, methotrexate, and paclitaxel, mitoxantrone, patupilone (epothilone B), epidermal-growth factor receptor (EGFR)-targeting monoclonal antibody 7A7.27, histone deacetylase inhibitors (vorinostat and romidepsin), the n3-polyunsaturated fatty acid docosahexaenoic acid, proteasome inhibitors (e.g. bortezomib), shikonin (the major constituent of the root of Lithospermum erythrorhizon,) and oncolytic viruses, such as TVec (talimogene laherparepvec).

17. Any of the preceding embodiments, further comprising radiation therapy.

18. Embodiment 12 wherein the one or more additional therapeutic treatments is radiation therapy.

19. Embodiment 19 comprises a method of treating a mammal who suffers from a cancer, wherein the cancer comprises a solid tumor, comprising administering intratumorally an effective amount of a composition comprising GLA, said composition comprising:

(a) GLA of the formula:

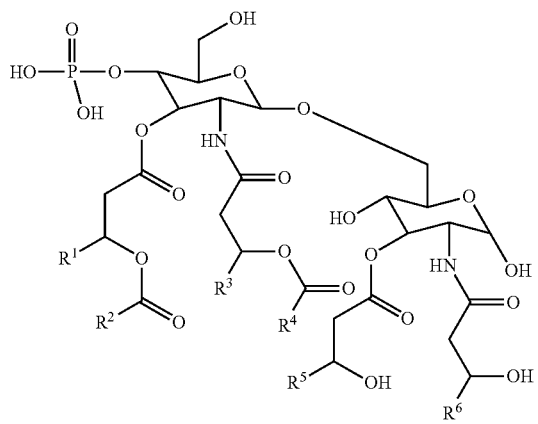

wherein:
$R^1$, $R^3$, $R^5$ and $R^6$ are undecyl and $R^2$ and $R^4$ are tridecyl
(b) a pharmaceutically acceptable carrier or excipient;
wherein the composition does not comprise antigen.

20. Embodiment 19, further comprising administering an immune checkpoint inhibitor.

21. Embodiment 19 further comprising administering an anti-CD40 antibody.

22. Embodiment 19-21, further comprising administering radiation therapy.

Other embodiments and uses will be apparent to one skilled in the art in light of the present disclosures. The following examples are provided merely as illustrative of various embodiments and shall not be construed to limit the invention in any way.

EXAMPLES

Example 1

In Vivo Anti Cancer Effect of GLA in a Murine B16 Melanoma Model

This Example demonstrates that GLA was effective at reducing tumor size and increasing percent survival as compared to saline treatment in a murine B16 melanoma tumor model.

The B16 murine melanoma model is an accepted animal model for both solid tumor formation as well as metastasis (see e.g., Curr Protoc Immunol. 2001 May; CHAPTER 20: Unit-20.1. doi:10.1002/0471142735.im2001s39). In this study, mice were inoculated subcutaneously with $3 \times 10^5$ B16 cells on Day minus 9 (n=10 per group). Mice were treated with either saline or 5 μg GLA-SE i.m. on Day 0, Day 9 and Day 14.

Figure 2:
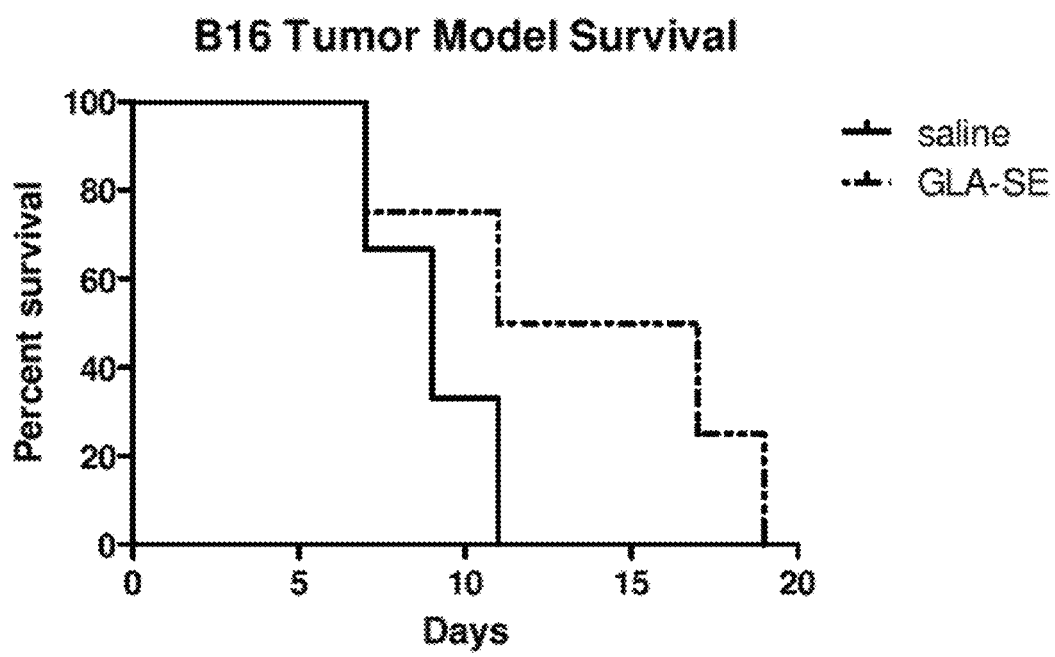
FIG. 2 is a survival curve showing that mice receiving GLA showed improved survival rate as compared to mice that received saline alone.

As shown in FIG. 1, GLA-SE treatment reduced tumor size in mice as compared to saline alone. As shown in FIG. 2, GLA-SE treatment increased percent survival in mice relative to saline alone.

Thus, these experiments demonstrate that GLA used alone has an anti-cancer effect in vivo in an accepted animal tumor model, after cancer has been established, and support the notion that GLA can be used as a monotherapy for the treatment of cancer.

Example 2

In Vivo Anti Cancer Effect of GLA in a Murine B16 Melanoma Model

Figure 3:
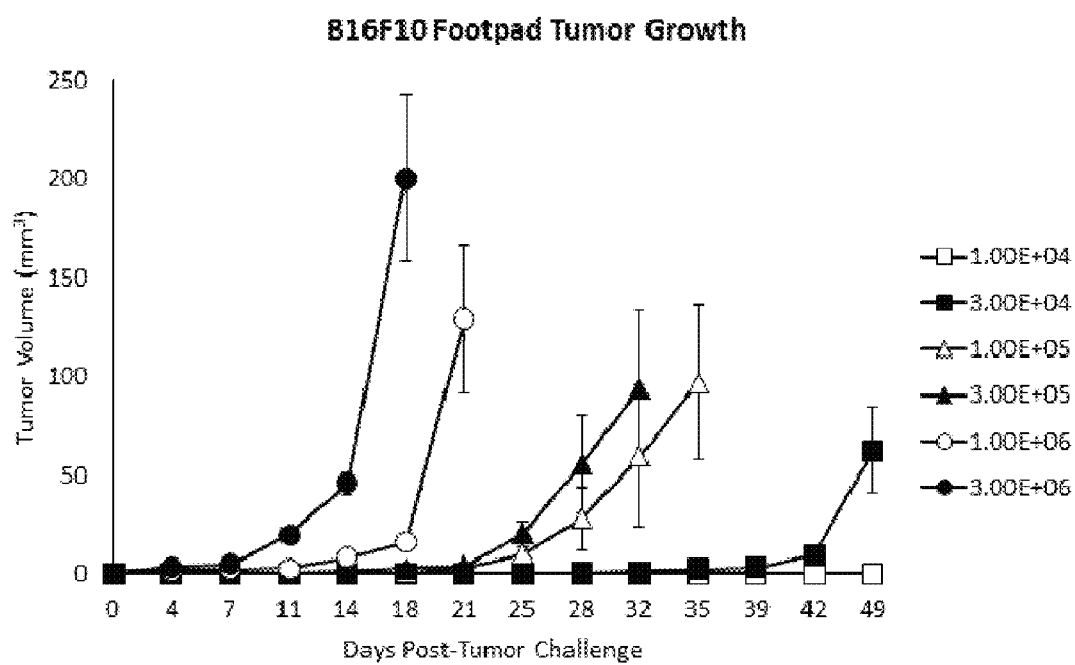
FIG. 3: Development of a murine B16F10 mouse footpad melanoma. B16F10 mouse footpad melanoma is a flexible therapeutic tumor model. B16F10 tumors are readily observable, therapeutic endpoint is set at tumor volume <100 mm² and animal health, 0.3E5 B16F10 cells is the recommended minimal tumor dose, depending on the number of cells injected, the therapeutic window can range between 14-40 days—Tumor dose can theoretically be increased to shorten the therapeutic window to less than 14 days.

Confirmatory experiments are performed using the B16 model as detailed below to further confirm whether GLA-SE administration diminishes B16F10 tumor growth in C57BL/6 mice. The B16 footpad melanoma model is well-established in the field. Tumor growth in the footpad is easily monitored because B16 melanoma cells are black. This model was established as shown in FIG. 3. In brief, high (1E6) or low (1E5) doses of B16F10 cells are injected as detailed further below into footpads of 8 wk/old C57BL/6J female mice. GLA-SE (5 μg/2% oil) is injected by various routes every 3 days, until mice are sacrificed (as tumor area reaches 100 mm$^2$)

Methods:
(Day -4): Culture B16F10 cells; Thaw cryopreserved cells in 37° C. water bath; B16F10 stock, 1 vial: B16-F10 ATCC Lot #59123188; count cells and seed @ 2-3E6 cells/T225 flask→Incubate @ 37° C., 5% CO2.

(Day 0): Harvest cells; Use cells in logarithmic growth phase (~50% confluent: 10-12E6 cells/T225 flask); Trypsinize and resuspend cells in appropriate volume of HBSS for doses outlined in Table 1 (generally not to exceed 50 ul volume); Transport harvested cells on ice to vivarium.

(Day 0): Inoculate mice; Mice: C57BL/6J females (8½ wk/old at injection). Anesthetize mice; ear punch mice for identification; inject, s.c., dose of cells as outlined in Table 1, per left mouse footpad; Return mice to cage.

(Day 0+3, onward): Administer GLA-SE or vehicle control (2% oil); Anesthetize mice; Inject GLA-SE (5 μg/2% oil) or vehicle control, s.c., into left mouse footpads (same footpads where the tumor cells were inoculated) or i.m. in thigh or s.c. at tail base; Return mice to cage.

Tumor growth is recorded 2-3 times per week. Mice are sacrificed via CO2 asphyxiation when tumors reach 100 mm$^2$.

The treatment groups for the experiment are outlined in Table 1 below:

TABLE 1

| | | | | | Treatment Groups | | |
|---|---|---|---|---|---|---|---|
| Group | Mouse # | Tumor Challenge (Day) | Tumor Type | Tumor Dose (Cells) | Vaccine Prime (Day)/route | Vaccine Type | Vaccine Dose (ug/% oil) |
| 037-Vehicle-1 | 1-10 | 0 | B16F10 | 1.0E5 | Every 3 d/foot pad | Vehicle (2% oil) | 0 |
| 037-GLA-1 | 11-20 | 0 | B16F10 | 1.0E5 | Every 3 d/foot pad | GLA-SE | 5.0 |
| 037-Vehicle-2 | 21-30 | 0 | B16F10 | 1.0E6 | Every 3 d/foot pad | Vehicle (2% oil) | 0 |
| 037-GLA-2 | 31-40 | 0 | B16F10 | 1.0E6 | Every 3 d/foot pad | GLA-SE | 5.0 |
| 037-Vehicle-3 | 41-50 | 0 | B16F10 | 1.0E5 | Every 3 d/i.m. | Vehicle (2% oil) | 0 |
| 037-GLA-3 | 51-60 | 0 | B16F10 | 1.0E5 | Every 3 d/i.m. | GLA-SE | 5.0 |
| 037-Vehicle-4 | 61-70 | 0 | B16F10 | 1.0E6 | Every 3 d/i.m. | Vehicle (2% oil) | 0 |

TABLE 1-continued

| | | Tumor Challenge (Day) | Tumor Type | Tumor Dose (Cells) | Vaccine Prime (Day)/route | Vaccine Type | Vaccine Dose (ug/% oil) |
|---|---|---|---|---|---|---|---|
| Group | Mouse # | | | | Treatment Groups | | |
| 037-GLA-4 | 71-80 | 0 | B16F10 | 1.0E6 | Every 3 d/i.m. | GLA-SE | 5.0 |
| 037-Vehicle-5 | 81-90 | 0 | B16F10 | 1.0E5 | Every 3 d/s.c, distal site (tail) | Vehicle (2% oil) | 0 |
| 037-GLA-5 | 91-100 | 0 | B16F10 | 1.0E5 | Every 3 d/s.c, distal site (tail) | GLA-SE | 5.0 |
| 037-Vehicle-6 | 101-110 | 0 | B16F10 | 1.0E6 | Every 3 d/s.c, distal site (tail) | Vehicle (2% oil) | 0 |
| 037-GLA-6 | 111-120 | 0 | B16F10 | 1.0E6 | Every 3 d/s.c, distal site (tail) | GLA-SE | 5.0 |

Additional experiments are performed with GLA injections every other day or every day. GLA-SE doses and/or formulation may also be modified.

In addition to the above experiments, further confirmatory experiments and characterization of GLA monotherapy in tumor models are carried out using a variety of different tumor model systems known to the skilled person. A variety of subcutaneous xenograft tumor models, orthotopic tumor models, metastatic tumor models and syngeneic mouse tumor models are used for further characterizing GLA as a monotherapy agent in cancer. As non-limiting examples, murine syngeneic model systems using H22, Hepa1-6, P388D1 or 5180 are used for evaluating GLA monotherapy in liver, leukemia and sarcoma tumor models. Various metastatic models are also used for evaluating GLA monotherapy and non-limiting examples include HCCLM3 (liver cancer; stomach and lymph node metastasis), MKN-45 (stomach cancer; liver and lymph node metastasis), HT-29 (colon cancer; met liver and lymph node), HCT-116 (colon cancer; met liver and lymph node), and PC-3 (prostate cancer; met bone). A variety of such animal models are commercially available, for example, from GenScript (Piscataway, N.J.) or Charles River Laboratories (Wilmington, Mass.). Additional models suitable for testing include, but are not limited to, models of melanoma, lung cancer, cervical cancer, ovarian cancer, uterine cancer, breast cancer, liver cancer, gastric cancer, prostate cancer, colon cancer, kidney cancer, bladder cancer, brain cancer, pancreatic cancer, leukemia and lymphoma.

In such models, tumor cells are inoculated by the appropriate route (e.g., s.c, i.v. or other route as generally accepted in the model) with established dosage of cells. GLA-SE is inoculated i.m. daily, every other day, every third day, once weekly or every other week Saline can be used as a control. In certain cases, it may be desirable to use SE as an additional control. Tumor growth and spread to local lymph nodes is assessed. The effect of GLA-SE on PBMCs are assessed for activation status by measuring cell surface markers on lymphocytes such as CD26, CD27, CD30, CDw137 (4-1BB), CD152 (CTLA-4), CD154 (gp39), CD134 (OX-40), CD95L (Fas ligand), CD45R/B220, and Ly-6E (TSA, sca-2) and/or cytokine expression levels such as IL-2, IFN-γ, IL-17, IL-4, IL-13, IL-10.

Example 3

In Vivo Anti Cancer Effect of GLA in a Murine B16 Melanoma Model

Additional experiments were carried out to confirm and further characterize the anti-cancer effect of GLA in a murine B16 melanoma model.

Figure 4:
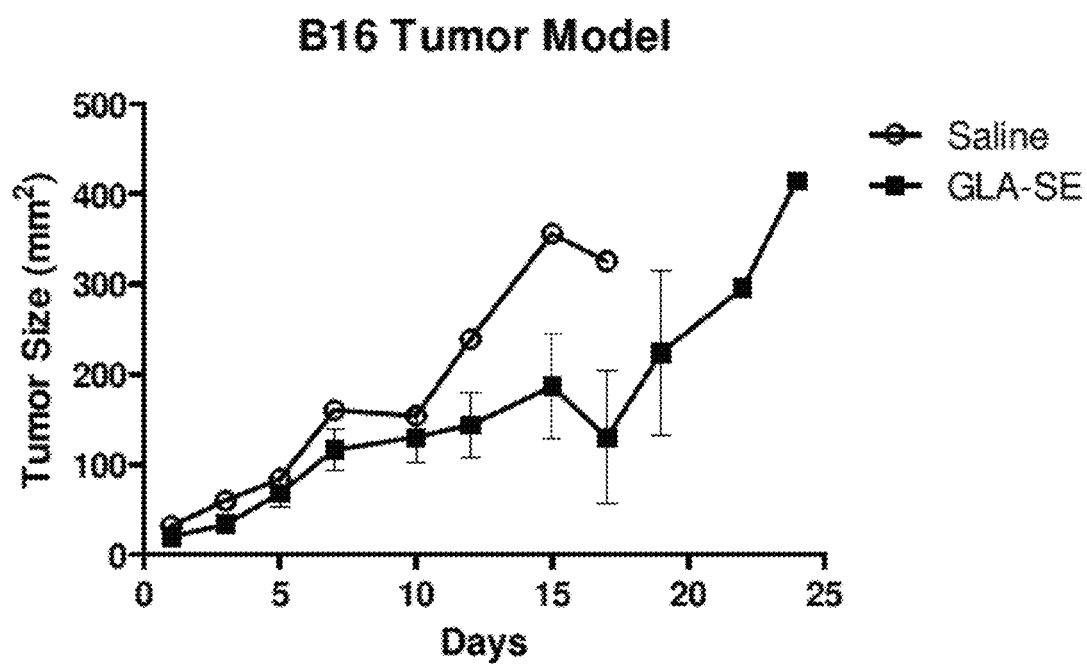
FIG. 4: GLA-SE administered by intramuscular route of administration significantly (p>0.008) modifies the growth kinetics of B16F10 tumor cells in BALB/c mouse. Statistical evaluation was performed using the Wilcoxon signed rank test.
Figure 5:
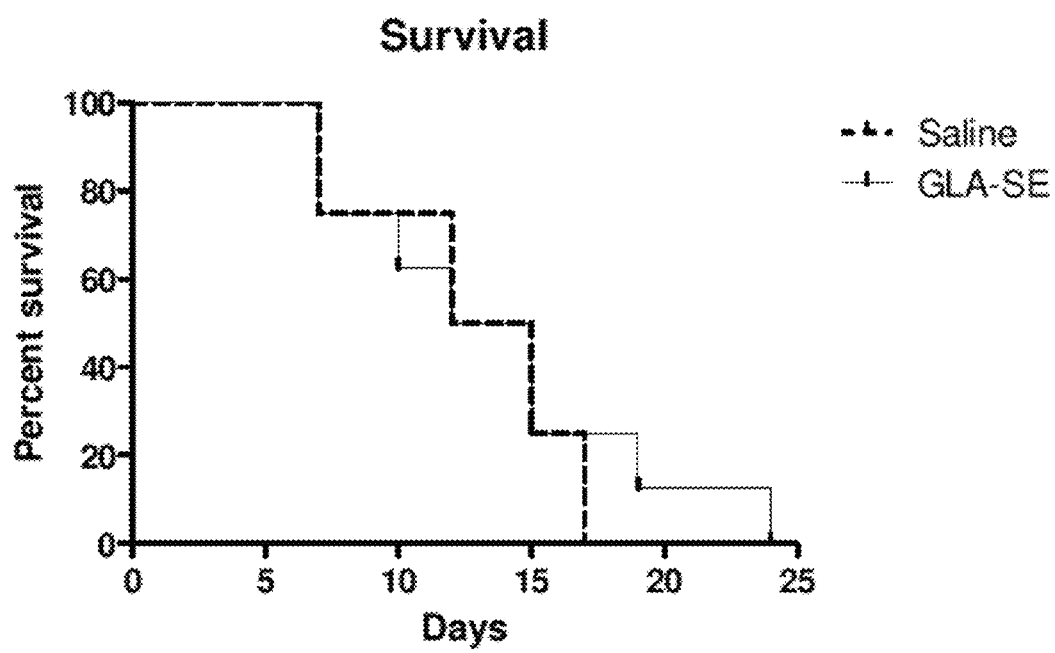
FIG. 5: GLA-SE administered by intramuscular route of administration significantly (p>0.03) increases the survival period of BALB/c mouse with B16F10 tumor burden. Statistical analysis was performed using the Gehan-Breslow Wilcoxon test.

Mice (n=10 per group) were inoculated into the flank with $5 \times 10^6$ B16F10 cells on study day minus 6 (Day −6). Mice were subsequently inoculated with either GLA-SE or placebo (saline) on days 0, day 5, day 15, and day 24. Tumor size of individual mice was measured every third day. Survival of mice, as measured by euthanasia when tumor size reached 400 mm² or when the tumor developed lesions, was also compared. Results of this study demonstrate that mice treated therapeutically with GLA-SE had significantly reduced tumor size (p>0.008) with clear differences between the groups observed at day 10 (FIG. 4). Mice treated with GLA-SE also had significantly (p>0.03) increased survival time with clear differences between groups observed after day 17 (FIG. 5).

Example 4

In Vivo Anti Cancer Effect of GLA in Murine Tumor Models

This Example demonstrates that GLA is effective at delaying tumor growth as compared to vehicle treatment in certain murine tumor models. The tumor models tested were B16 melanoma, CT26 colon cancer, 4T1 breast cancer, and P815 mastocytoma.

In this study, on Day 0, the following groups of mice (n=5 per group) were inoculated with the corresponding number of tumor cells: C57BL/6, $5 \times 10^5$ B16F10 cells, subcutaneously in the right footpad; BALB/c, $5 \times 10^5$ CT26 cells, subcutaneously in the right footpad; BALB/c, $1 \times 10^5$ 4T1 cells in the 4$^{th}$ right mammary fat pad; DBA/2, $1 \times 10^4$ P815 cells, subcutaneously in the right flank. Mice were given intramuscular (i.m.) or intratumoral (i.t.) administrations of vehicle control (2% SE) or 5 µg GLA-SE/2% SE starting on Day 4 and every 3-4 days thereafter until the end of study.

Figure 6:
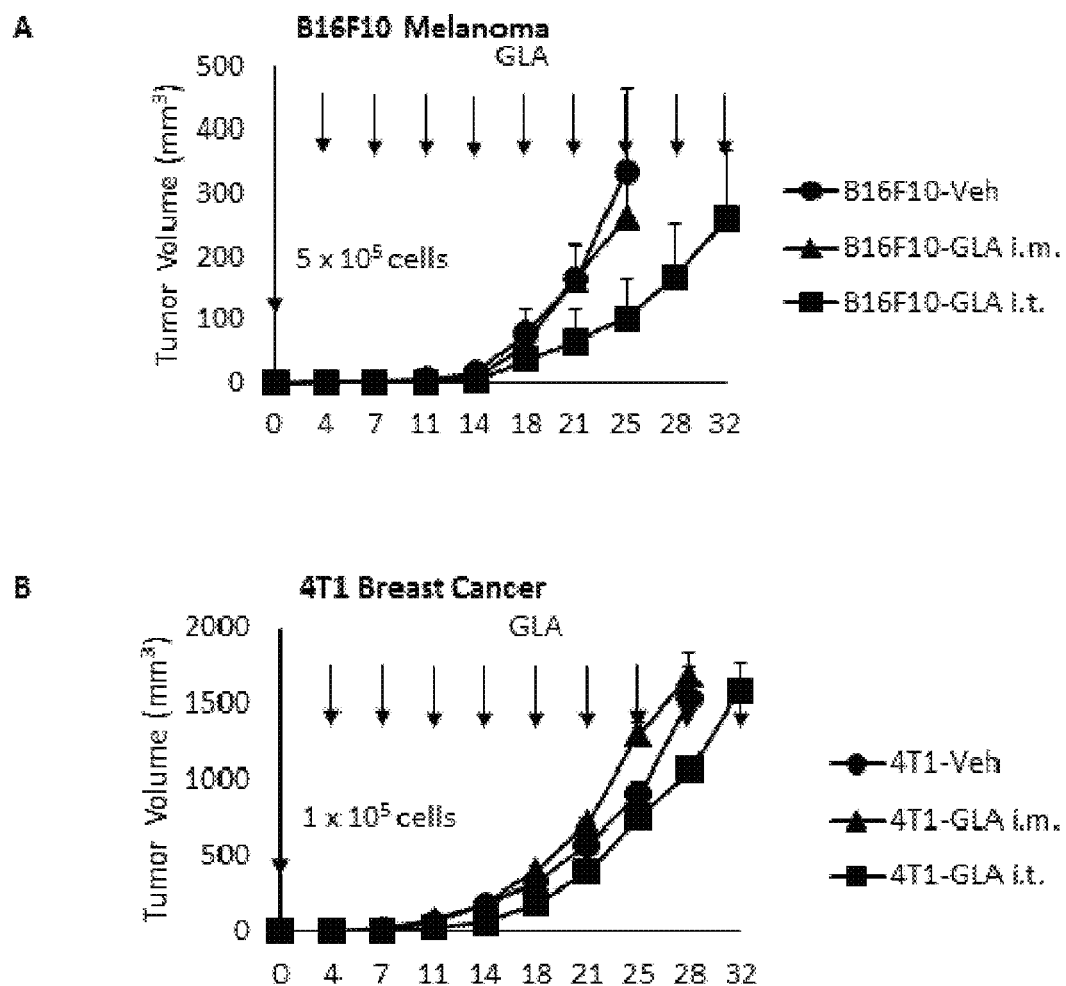
FIG. 6 is a graph of tumor size over time in mice administered vehicle (2% SE) or GLA-SE intramuscularly (i.m.) or intratumorally (i.t.) following inoculation of tumor cells. Student's t-test was used for inter-group comparisons: *p<0.05.
Figure 6:
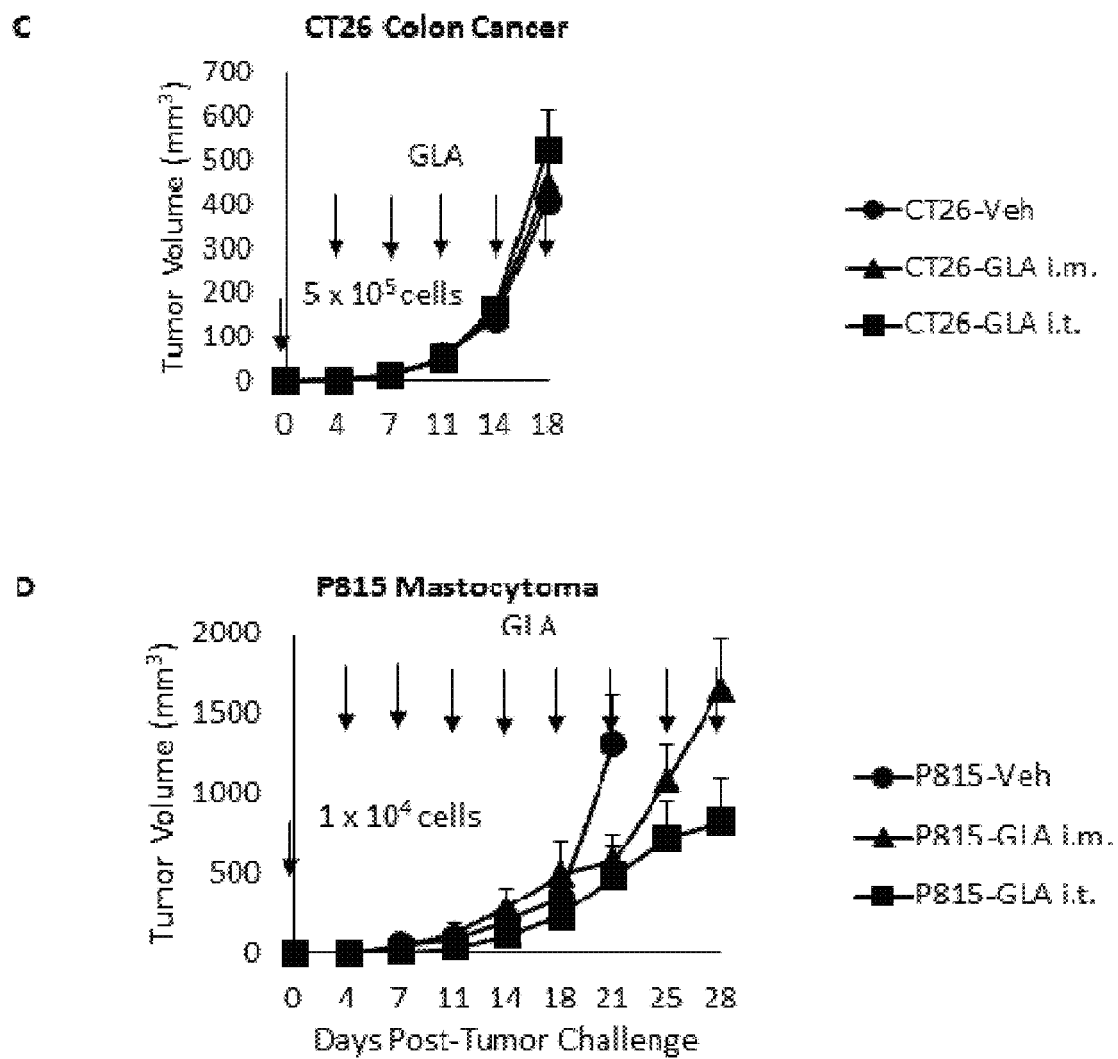

As shown in FIG. 6, i.t. administration of GLA-SE delayed tumor growth in mice in multiple murine cancer models more effectively than i.m. administration. Intratumoral administration of GLA-SE delayed B16F10 and P815 tumor growth in a statistically significant manner as compared to vehicle alone. Intratumoral administration of GLA-SE also delayed 4T1 tumor growth although this was not statistically significant. Intratumoral injection was more effective than i.m. in these three tumor models. While i.m. administration of GLA-SE exhibited no effect on B16F10 tumor growth, it slightly delayed both 4T1 and P815 tumor growth. GLA-SE administered i.t. or i.m. exhibited no effect on CT26 tumor growth.

The above data demonstrate that GLA as a single agent has a statistically significant anti-cancer effect in vivo in accepted animal tumor models, after cancer has been established, and support the notion that GLA can be used as a monotherapy for the treatment of cancer.

Example 5

In Vivo Anti Cancer Effect of GLA in Combination with Checkpoint Inhibitors in the B16F10 Murine Tumor Model This example demonstrates that the addition of certain immune checkpoint inhibitors (CPIs) in the presence of GLA further delayed tumor growth as compared to vehicle treatment.

Figure 7:
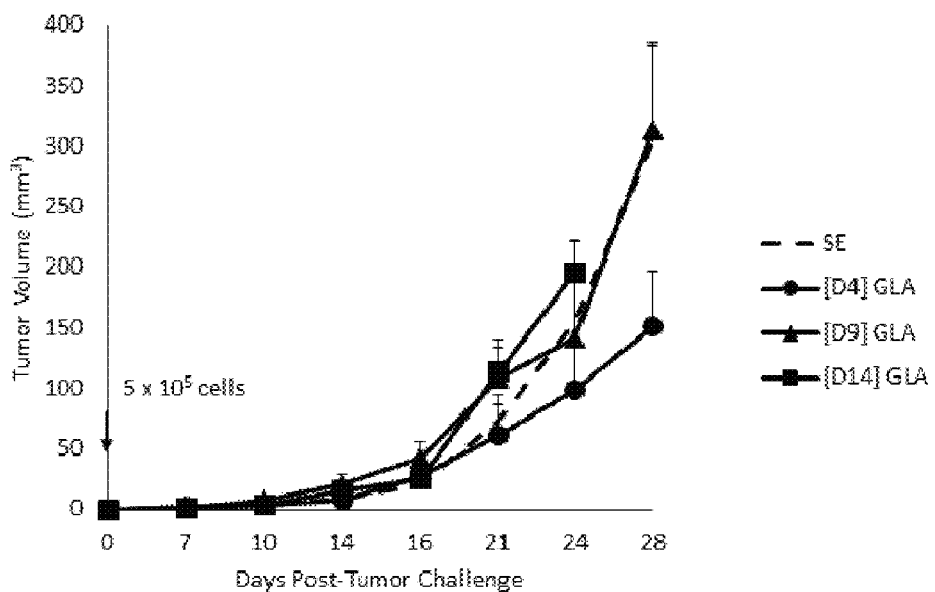
FIG. 7: Therapeutic Efficacy of GLA+/−a checkpoint inhibitor in the B16F10 mouse melanoma model. A is a graph of tumor size over time in tumor-bearing mice administered GLA-SE (i.t.) or 2% SE vehicle control starting on Day 4, 9, or 14 post-tumor injection. B is a graph of tumor size over time in tumor-bearing mice administered GLA-SE (i.t.) or 2% SE vehicle control plus an immune checkpoint inhibitor (anti-PDL1, anti-PD1, anti-CTLA4, or LTF2 control antibody; i.p.) starting on Day 4 post-tumor injection. Student's t-test was used for inter-group comparisons: *p=0.03; **p=0.005.
Figure 7:
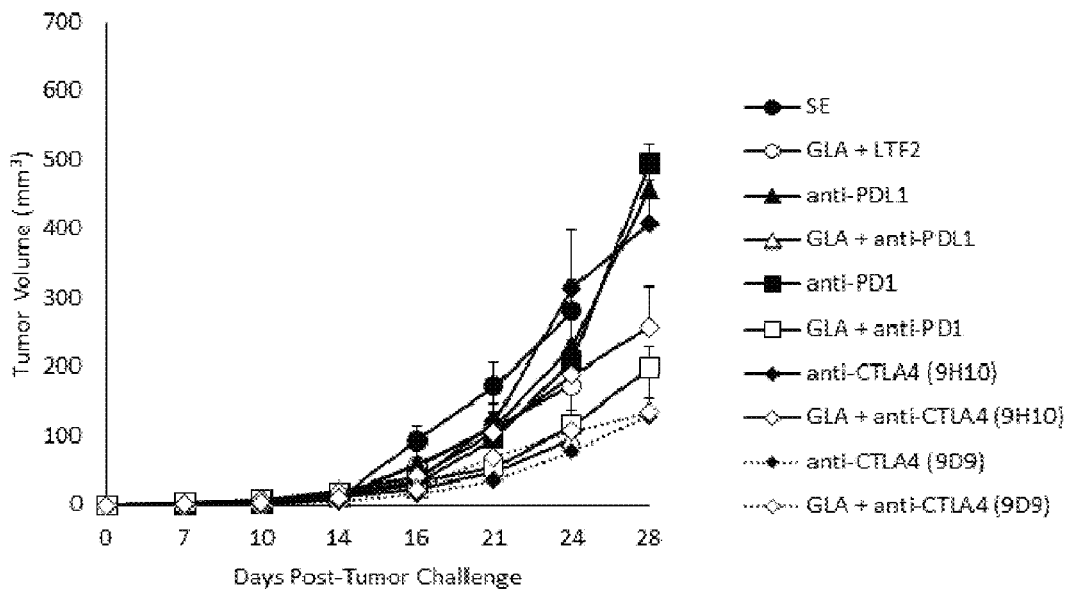

To determine the optimal time to begin GLA administration, female C57BL/6 mice (n=5 per group) were inoculated with $5 \times 10^5$ B16F10 cells, subcutaneously in the right footpad on Day 0. Mice were given intratumoral (i.t.) administrations of 5 μg GLA-SE/2% SE (or 2% SE vehicle control) on Day 4, Day 9, or Day 14, and every 3-4 days thereafter until the end of study. When GLA administration began within 4 days (but not 9 or 14 days) post-tumor injection, it delayed B16F10 tumor growth in mice (FIG. 7A).

To determine whether the addition of a CPI further delayed tumor growth, female C57B1/6 mice (n=5 per group) were inoculated with $5 \times 10^5$ B16F10 cells, subcutaneously in the right footpad on Day 0. Mice were given i.t. administrations of 5 μg GLA-SE/2% SE (or 2% SE vehicle control) plus intraperitoneal (i.p.) administrations of a CPI [anti-PDL1, anti-PD1, anti-CTLA4 (clone 9H10), anti-CTLA4 (clone 9D9), or LTF2 control antibody] at 100 μg starting on Day 4 and every 3-4 days thereafter until the end of study. GLA alone delayed B16F10 tumor growth in mice (FIG. 7B). The addition of anti-PDL1, anti-PD1 (p=0.03), or anti-CTLA 4 (clone 9D9; p=0.005) in the presence of GLA further delayed tumor growth as compared to SE vehicle alone. Anti-CTLA4 (clone 9H10) exhibited no additive effect on B16F10 tumor growth, while clone 9D9 exhibited therapeutic effect on its own, suggesting therapeutic efficacy varies between different antibody clones.

The above data demonstrate that the addition of an immune checkpoint inhibitor in the presence of GLA statistically significantly enhances the overall anti-tumor effect in vivo.

Example 6

In Vivo Anti Cancer Effect of Gla in Combination with the Anti-CD40 Co-Stimulatory Antibody in the B16F10 Murine Tumor Model This example demonstrates that the addition of anti-CD40 in the presence of GLA further delayed tumor growth as compared to vehicle treatment.

CD40 is expressed on antigen-presenting cells and is an important co-stimulatory molecule for the activation of T cells, B cells, dendritic cells, and macrophages. Anti-CD40 has previously been shown to exhibit anti-tumor effects via activation of the innate immune responses, such as mobilizing macrophages (Buhtoiarov I N, et al. J Immunother 2005; 174:6013-6022).

Figure 8:
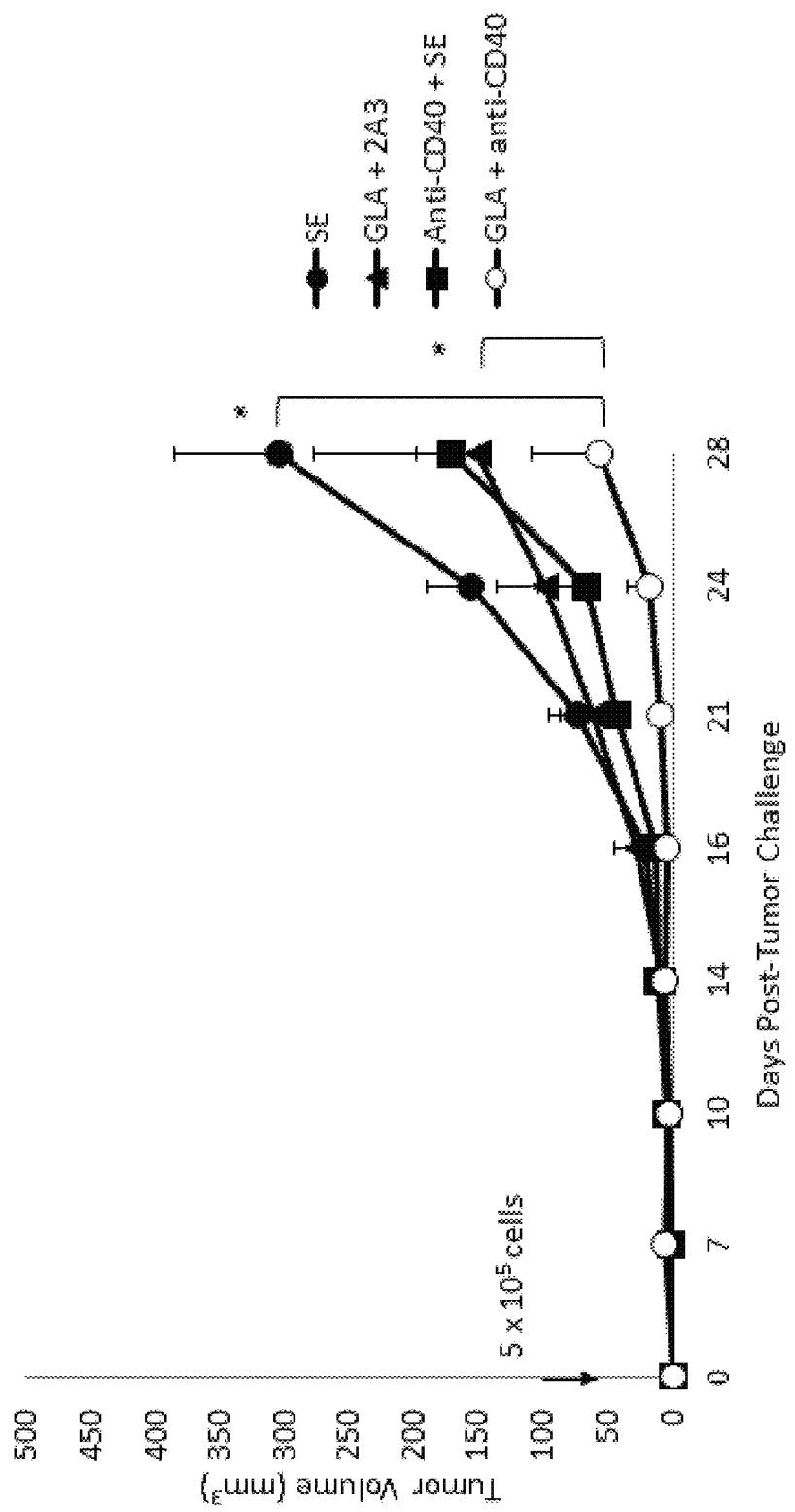
FIG. 8: Therapeutic Efficacy of GLA+/−anti-CD40 in the B16F10 mouse melanoma model. A is a graph of tumor size over time in tumor-bearing mice administered GLA-SE (i.t.) or 2% SE vehicle control plus anti-CD40 antibody (i.p.) starting on Day 4 post-tumor injection. B is a graph of tumor size over time in tumor-bearing mice administered GLA-SE (i.t.) or 2% SE vehicle control on Day 8 and 15 post-tumor injection, plus anti-CD40 (i.t.) on Day 5 and 12 post-tumor injection. Student's t-test was used for inter-group comparisons: *p=0.03; ns=not significant.
Figure 8:
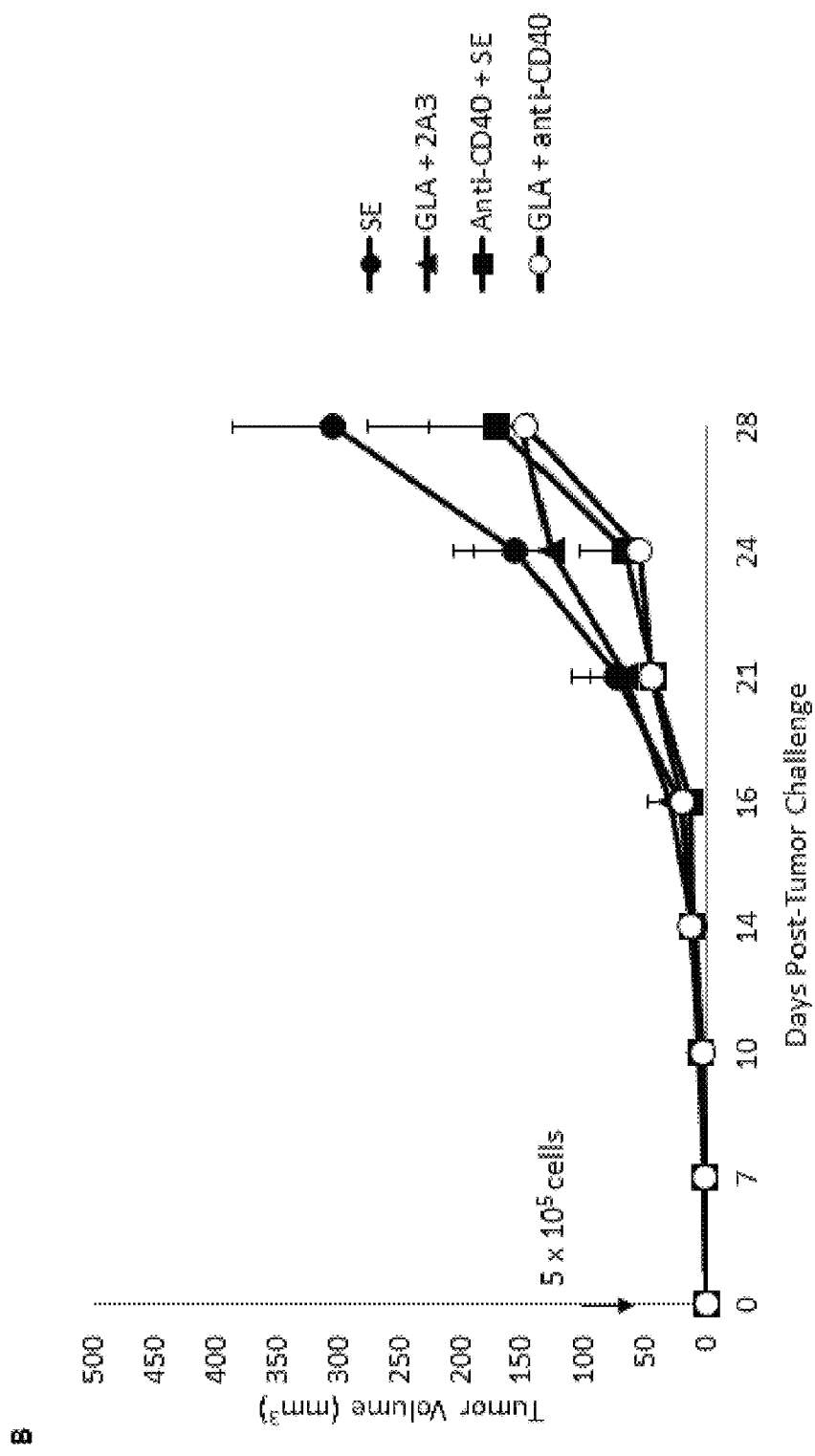

To determine whether the addition of anti-CD40 further delayed tumor growth, female C57B1/6 mice (n=5 per group) were inoculated with $5 \times 10^5$ B16F10 cells, subcutaneously in the right footpad on Day 0. Mice were given i.t. administrations of 5 μg GLA-SE/2% SE (or 2% SE vehicle control) plus i.p. administrations of anti-CD40 (or 2A3 control antibody) at 100 μg, starting on Day 4 and every 3-4 days thereafter until the end of study (FIG. 8A). Either GLA or anti-CD40 alone delayed B16F10 tumor growth in mice. The combination of GLA and anti-CD40 further delayed tumor growth and the delay was statistically significant as compared to GLA-SE with control antibody as well as compared to SE control.

To determine whether anti-CD40 exerted anti-tumor effects in the tumor microenvironment, tumor-bearing mice were given i.t. administrations of 2 μg GLA-SE/2% SE (or 2% SE vehicle control) on Day 8 and 15 post-tumor injection and i.t. administrations of 50 μg anti-CD40 (or 2A3 control antibody) on Day 5 and 12 post-tumor injection (FIG. 8B). Suboptimal doses for GLA and anti-CD40 were given to avoid masking of a possible synergistic effect of the combination. Although either GLA or anti-CD40 alone delayed tumor growth, the combination of GLA and anti-CD40, when injected locally into the tumor, did not further delay the growth. The differences in therapeutic efficacy observed between i.p. and i.t. administrations of anti-CD40 suggest 1) therapeutic regimen or 2) targeting of systemic or local activation of innate immune response may be key factors to inducing anti-tumor effects.

The above data demonstrate that the systemic addition of anti-CD40 (i.p.) statistically significantly enhances the anti-tumor effect of intratumorally applied GLA in vivo.

Example 7

In Vivo Anti Cancer Effect of Intratumoral Injection of GLA-SE in Merkel Cell Carcinoma in Human Patients This Example describes preliminary observations from the first human patients dosed with intratumoral GLA-SE.

Merkel cell carcinoma (MCC) is a rare but highly aggressive skin cancer with a much higher mortality rate than malignant melanoma. Despite the use of surgery or radiation for patients with loco-regional MCC, recurrence rates are high and there is no established adjuvant therapy. Merkel cell polyomavirus (MCPyV) is a common virus present in eight out of ten MCCs and is thought to be involved in the etiology of the disease.

Three MCC patients have been treated as part of a Phase I clinical trial entitled, "A Proof of Concept Clinical Trial of Intratumoral Injection of GLA-SE in Patients with Merkel Cell Carcinoma." Patients included in the study had biopsy-confirmed Merkel cell carcinoma with metastatic or loco-regional disease. Patients had to have at least one injectable lesion, defined as an easily palpable superficial lesion (cutaneous, subcutaneous or lymph nodal) that can be accurately localized, stabilized by palpation, and is superficial enough to enable intratumoral (i.t.) injection. Following enrollment, patients were injected with 5 ug GLA-SE (1 mL) directly into the tumor(s) two to three times, as detailed in the protocol.

One patient with loco-regional disease received 2 doses of GLA-SE on days 1 and 8 i.t. in a femoral lymph node. Surprisingly, at surgical resection on day 21, the patient was found to have completely responded in the treated tumor with no evidence of cancer by pathologic review of the excised lesion. Initial observations indicate an enrichment of tumor infiltrating lymphocytes (TILs). As part of standard of care, the patient will be receiving post-surgical adjuvant radiation therapy.

Two other patients who presented with metastatic disease were also treated. One had no apparent response and disease progressed during the first cycle. This patient is now off study.

The other patient also presented with metastatic disease and had inflammation at the two sites of injection after the third dose. No information about a non-injected lesion was provided and no additional information is yet available for this patient.

This Example describes for the first time, results in humans from a Phase I clinical trial investigating i.t. injection of GLA in the absence of exogenous antigen. It was entirely unexpected to see a complete response in this type of cancer that has historically been so resistant to treatment. Although these results are preliminary and the primary response is an observation in a single patient, they suggest that GLA-SE injected i.t. has an anti-cancer effect and further support the notion that GLA can be used without antigen for the treatment of cancer.

Example 8

Intratumoral GLA, Anti-CTLA-4 and Rituximab for the Treatment of Follicular Low Grade NHL This Example describes the investigation of the effect of GLA in combination with anti-CTLA 4 and rituximab antibodies for the treatment of cancer.

Patients are treated at a single tumor site with intratumoral injection of GLA, anti-CTLA-4 and rituximab at a dose repeated every weak for 8-10 weeks. Two different dose levels are examined. A Phase II trial is conducted for randomized investigation of low versus high dose of GLA with fixed doses of anti-CTLA4 and rituximab. Staging studies are conducted at baseline and weekly for eight weeks. Endpoints include direct response at the injected site, abscopal response distally, overall response (complete responses/partial response), time to progression/progression free survival and time to next treatment.

These studies will test whether the combination of GLA with anti-CTLA4 antibodies and antibodies that increase ADCC uptake of tumor antigens in dendritic cells or other antigen presenting cells (e.g., rituximab) enhances the anti-tumor immune response and provides therapeutic benefit for cancer patients.

The various embodiments described above can be combined to provide further embodiments. All U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified if necessary to employ concepts of the various patents, applications, and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method of treating a mammal who suffers from cancer, comprising administering by intratumoral injection an effective amount of a composition comprising:

(a) GLA of the formula:

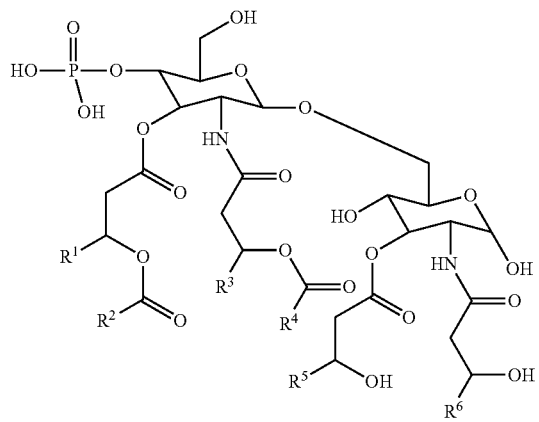

wherein:

$R^1$, $R^3$, $R^5$ and $R^6$ are undecyl; and $R^2$ and $R^4$ are tridecyl; and (b) a pharmaceutically acceptable carrier or excipient; wherein the composition does not comprise antigen.

2. The method of claim 1 wherein the mammal is human.

3. The method of claim 1, wherein the composition is an aqueous formulation.

4. The method of claim 1, wherein the composition is in the form of an oil-in-water emulsion, a water-in-oil emulsion, liposome, micellar formulation, or a microparticle formulation.

5. The method of claim 1, wherein the cancer comprises a solid tumor.

6. The method of claim 5, wherein the solid tumor is a carcinoma, a sarcoma or a lymphoma.

7. The method of claim 5, wherein the solid tumor is a primary solid tumor.

8. The method of claim 5, wherein the solid tumor is a secondary solid tumor.

9. The method of claim 1, wherein the cancer is selected from the group consisting of, melanoma, Merkel cell carcinoma, lung cancer, cervical cancer, ovarian cancer, uterine cancer, breast cancer, liver cancer, gastric cancer, prostate cancer, colon cancer, kidney cancer, bladder cancer, brain cancer, and pancreatic cancer.

10. The method of claim 1, wherein the composition is administered in conjunction with one or more additional therapeutic agents or treatments.

11. The method of claim 10, wherein the therapeutic agent is an immune checkpoint inhibitor.

12. The method of claim 10, wherein the therapeutic agent is an antibody that activates a co-stimulatory pathway.

13. The method of claim 12, wherein the antibody is an anti-CD40 antibody.

14. The method of claim 10, wherein the therapeutic agent is a cancer therapeutic agent.

15. The method of claim 14, wherein the cancer therapeutic agent is selected from the group consisting of taxotere, carboplatin, trastuzumab, epirubicin, cyclophosphamide, cisplatin, docetaxel, doxorubicin, etoposide, 5-FU, gemcitabine, methotrexate, and paclitaxel, mitoxantrone, epothilone B, epidermal-growth factor receptor (EGFR)-targeting monoclonal antibody 7A7.27, vorinostat, romidepsin, docosahexaenoic acid, bortezomib, shikonin and an oncolytic virus.

16. The method of claim 10 wherein the one or more additional therapeutic treatments is radiation therapy.

17. The method of claim 1 wherein 0.1-10 µg of GLA is present in the composition.

18. A method of treating a human who suffers from Merkel cell carcinoma, comprising administering by intratumoral injection into the Merkel cell carcinoma an effective amount of a composition comprising 0.1-10 µg of GLA of the formula:

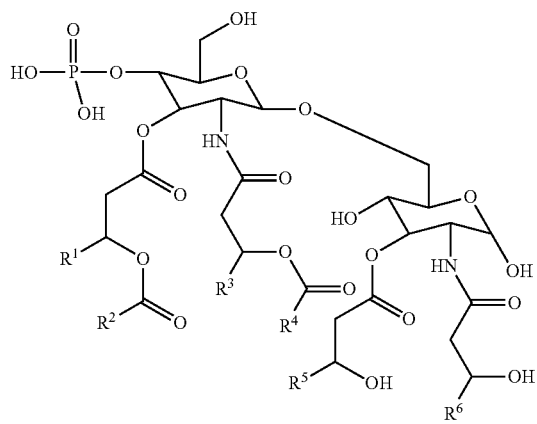

wherein:
$R^1$, $R^3$, $R^5$ and $R^6$ are undecyl; and
$R^2$ and $R^4$ are tridecyl; and
 (b) a pharmaceutically acceptable carrier or excipient; wherein the composition does not comprise antigen, and wherein the composition is in the form of an oil-in-water emulsion.

* * * * *